(12) United States Patent
Ghebremeskel et al.

(10) Patent No.: US 9,980,974 B2
(45) Date of Patent: *May 29, 2018

(54) PROSTAMIDE-CONTAINING INTRAOCULAR IMPLANTS AND METHODS OF USE THEREOF

(71) Applicant: Allergan, Inc., Irvine, CA (US)

(72) Inventors: Alazar N. Ghebremeskel, Irvine, CA (US); Michael R. Robinson, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/350,471

(22) Filed: Nov. 14, 2016

(65) Prior Publication Data

US 2017/0056412 A1 Mar. 2, 2017

Related U.S. Application Data

(63) Continuation of application No. 14/529,526, filed on Oct. 31, 2014, now Pat. No. 9,492,316.

(60) Provisional application No. 61/898,241, filed on Oct. 31, 2013.

(51) Int. Cl.
| | |
|---|---|
| A61K 9/52 | (2006.01) |
| A61K 9/58 | (2006.01) |
| A61K 31/765 | (2006.01) |
| A61K 31/5575 | (2006.01) |
| A61F 9/00 | (2006.01) |
| A61K 31/165 | (2006.01) |
| A61K 9/00 | (2006.01) |
| A61K 47/10 | (2017.01) |
| A61K 47/34 | (2017.01) |
| A61K 9/16 | (2006.01) |

(52) U.S. Cl.
CPC ........ *A61K 31/5575* (2013.01); *A61F 9/0017* (2013.01); *A61K 9/0051* (2013.01); *A61K 9/1647* (2013.01); *A61K 31/165* (2013.01); *A61K 47/10* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 3,749,776 | A | 7/1973 | Eakins et al. |
| 4,853,224 | A | 8/1989 | Wong |
| 4,994,274 | A | 2/1991 | Chan et al. |
| 4,997,652 | A | 3/1991 | Wong |
| 5,028,624 | A | 7/1991 | Chan et al. |
| 5,034,413 | A | 7/1991 | Chan et al. |
| 5,164,188 | A | 11/1992 | Wong |
| 5,443,505 | A | 8/1995 | Wong et al. |
| 5,446,041 | A | 8/1995 | Chan et al. |
| 5,516,522 | A | 5/1996 | Peyman et al. |
| 5,545,665 | A | 8/1996 | Burk |
| 5,585,401 | A | 12/1996 | Brandt et al. |
| 5,688,819 | A | 11/1997 | Woodward et al. |
| 5,716,981 | A | 2/1998 | Hunter et al. |
| 5,741,810 | A | 4/1998 | Burk |
| 5,834,498 | A | 11/1998 | Burk |
| 6,124,344 | A | 9/2000 | Burk |
| 6,294,563 | B1 | 9/2001 | Garst |
| 6,309,669 | B1 | 10/2001 | Setterstrom et al. |
| 6,395,787 | B1 | 5/2002 | Woodward et al. |
| 6,403,649 | B1 | 6/2002 | Woodward et al. |
| 6,602,900 | B2 | 8/2003 | Burk |
| 6,899,717 | B2 | 5/2005 | Weber et al. |
| 7,799,336 | B2 | 9/2010 | Hughes et al. |
| 7,993,634 | B2 | 8/2011 | Hughes et al. |
| 8,147,865 | B2 | 4/2012 | Huang et al. |
| 8,206,736 | B2 | 6/2012 | Hughes |
| 8,206,737 | B2 | 6/2012 | Hughes |
| 8,231,892 | B2 | 7/2012 | Lyons et al. |
| 8,445,027 | B2 | 5/2013 | Hughes |
| 8,647,659 | B2 | 2/2014 | Robinson et al. |
| 9,061,065 | B2 | 6/2015 | Robinson et al. |
| 9,492,316 | B2 * | 11/2016 | Ghebremeskel ...... A61F 9/0017 |
| 2002/0032201 | A1 | 3/2002 | Olejnik et al. |

(Continued)

FOREIGN PATENT DOCUMENTS

| | | |
|---|---|---|
| EP | 0251680 | 1/1988 |
| EP | 1541151 | 6/2005 |

(Continued)

OTHER PUBLICATIONS

Brubaker, Richard et al, Effects of AGN 192024, a new Ocular Hypotensive Agent, on Aqueous Dynamics, American journal of Ophthalmology, 2001, 19-24, 131(1).
Cantor, LB, An Update on Bimatoprost in Glaucoma Therapy, Expert Opin Pharmacother, Dec. 2002, 1753-1762, 3 (12).
Caprioli, J, et al., Intraocular Pressure Fluctuation, Ophthalmology, 2008, 1123-1129, vol. 115, American Academy of Ophthalmology.
Coleman, Anne et al., A 3-Month Randomized Controlled Trial of Bimatoprost (LUMIGAN) Versus Combined Timolol and Dorzolamide (Cosopt) in Patients with Glaucoma or Ocular Hypertension, Ophthalmology, 2003, 2362-8, 110-12.
Collaborative Normal-Tension Glaucoma Study Group, The Effectiveness of Intraocular Pressure Reduction in the Treatment of Normal-Tension Glaucoma, American Journal of Ophthalmology, 1998, 498-505, vol. 126, No. 4, Elsevier Schience Inc.

(Continued)

*Primary Examiner* — Abigail Vanhorn
(74) *Attorney, Agent, or Firm* — Laura L. Wine

(57) ABSTRACT

Prostamide-containing intraocular implants that biodegrade in the eye and that are effective for reducing intraocular pressure in an eye for a sustained period. The implants generally contain a prostamide, such as bimatoprost, and at least three distinct biodegradable polymers selected from polylactide and poly(lactide-co-glycolide) polymers and are optimized for placement in and compatibility with the anterior chamber of the eye, particularly the anterior chamber angle. Methods for making and using the implants to reduce ocular hypertension and intraocular pressure in a patient are described.

7 Claims, 8 Drawing Sheets

(56) References Cited

U.S. PATENT DOCUMENTS

| | | |
|---|---|---|
| 2002/0035264 A1 | 3/2002 | Kararli |
| 2002/0198249 A1 | 12/2002 | Burk |
| 2003/0069560 A1 | 4/2003 | Adamis et al. |
| 2003/0220376 A1 | 11/2003 | Masferrer |
| 2004/0054374 A1 | 3/2004 | Weber et al. |
| 2004/0127843 A1 | 7/2004 | Tu |
| 2004/0151753 A1 | 8/2004 | Chen et al. |
| 2004/0175410 A1 | 9/2004 | Ashton |
| 2005/0228185 A1 | 10/2005 | Donde |
| 2005/0244458 A1 | 11/2005 | Huang et al. |
| 2005/0244463 A1 | 11/2005 | Huang et al. |
| 2005/0244464 A1 | 11/2005 | Hughes |
| 2005/0244467 A1 | 11/2005 | Nivaggioli et al. |
| 2005/0244468 A1 | 11/2005 | Huang et al. |
| 2005/0244469 A1 | 11/2005 | Whitcup et al. |
| 2005/0282902 A1 | 12/2005 | Chen et al. |
| 2006/0035961 A1 | 2/2006 | Donde et al. |
| 2006/0106088 A1 | 5/2006 | Donde et al. |
| 2006/0111430 A1 | 5/2006 | Donde et al. |
| 2006/0173060 A1 | 8/2006 | Chang et al. |
| 2006/0182781 A1 | 8/2006 | Hughes |
| 2006/0210604 A1 | 9/2006 | Dadey |
| 2006/0233859 A1 | 10/2006 | Whitcup et al. |
| 2006/0246145 A1 | 11/2006 | Chang |
| 2007/0010495 A1 | 1/2007 | Donde |
| 2007/0014848 A1 | 1/2007 | Buchholz et al. |
| 2007/0031472 A1 | 2/2007 | Huang |
| 2007/0066541 A1 | 3/2007 | Hughes et al. |
| 2007/0099984 A1 | 5/2007 | Burk et al. |
| 2007/0212395 A1 | 9/2007 | Donello et al. |
| 2007/0219265 A1 | 9/2007 | Old et al. |
| 2007/0224246 A1 | 9/2007 | Hughes et al. |
| 2007/0249595 A1 | 10/2007 | Ries et al. |
| 2007/0259836 A1 | 11/2007 | Donde et al. |
| 2007/0259947 A1 | 11/2007 | Donde et al. |
| 2007/0287742 A1 | 12/2007 | Old et al. |
| 2007/0293873 A1 | 12/2007 | Chang |
| 2007/0298073 A1 | 12/2007 | Whitcup et al. |
| 2007/0298074 A1 | 12/2007 | Robinson et al. |
| 2008/0033351 A1 | 2/2008 | Trogden |
| 2008/0058414 A1 | 3/2008 | Old et al. |
| 2008/0097335 A1 | 4/2008 | Trogden et al. |
| 2008/0131481 A1 | 6/2008 | Hughes |
| 2008/0131482 A1 | 6/2008 | Hughes |
| 2008/0131484 A1 | 6/2008 | Robinson |
| 2008/0145403 A1 | 6/2008 | Spada |
| 2008/0145407 A1 | 6/2008 | Huang et al. |
| 2008/0255220 A1 | 10/2008 | Old |
| 2008/0292679 A1 | 11/2008 | Lyons |
| 2009/0081277 A1 | 3/2009 | Robinson et al. |
| 2009/0082863 A1 | 3/2009 | Schieber |
| 2009/0318404 A1 | 12/2009 | Old |
| 2010/0074957 A1 | 3/2010 | Robinson et al. |
| 2010/0098772 A1 | 4/2010 | Robinson et al. |
| 2010/0104654 A1 | 4/2010 | Robinson et al. |
| 2010/0124565 A1 | 5/2010 | Spada et al. |
| 2010/0247606 A1 | 9/2010 | Robinson |
| 2010/0278898 A1 | 11/2010 | Hughes et al. |
| 2011/0077229 A1 | 3/2011 | Edelman et al. |
| 2011/0091520 A1 | 4/2011 | Huang et al. |
| 2011/0182966 A1 | 7/2011 | Robinson |
| 2011/0250285 A1 | 10/2011 | Hughes |
| 2012/0122821 A1 | 5/2012 | Huang |
| 2012/0219611 A1 | 8/2012 | Hughes |
| 2012/0238633 A1 | 9/2012 | Hughes |
| 2012/0245505 A1 | 9/2012 | Robinson et al. |
| 2012/0270915 A1 | 10/2012 | Woodward et al. |
| 2012/0276184 A1 | 11/2012 | Ghebremeskel et al. |
| 2012/0276186 A1 | 11/2012 | Ghebremeskel et al. |
| 2013/0017268 A1 | 1/2013 | Robinson et al. |
| 2013/0071349 A1 | 3/2013 | Robinson et al. |
| 2013/0236557 A1 | 9/2013 | Hughes et al. |

FOREIGN PATENT DOCUMENTS

| | | |
|---|---|---|
| WO | 1994-014417 | 7/1994 |
| WO | 1995-018102 | 7/1995 |
| WO | 2000-037056 | 6/2000 |
| WO | 2002-002076 | 1/2002 |
| WO | 2002-043785 | 6/2002 |
| WO | 2003024420 A1 | 3/2003 |
| WO | 2005-107727 | 11/2005 |
| WO | 2005-110368 | 11/2005 |
| WO | 2005-110424 | 11/2005 |
| WO | 2005110380 A1 | 11/2005 |
| WO | 2008-070402 | 6/2008 |
| WO | 2008-079674 | 7/2008 |
| WO | 2009-143288 | 11/2009 |
| WO | 2010-048086 | 4/2010 |
| WO | 2010-056598 | 5/2010 |
| WO | 2010-062523 A2 | 6/2010 |
| WO | 2010-111449 | 9/2010 |
| WO | 2011-075481 | 6/2011 |
| WO | 2011-091205 | 7/2011 |
| WO | 2011-109384 | 9/2011 |
| WO | 2011-130462 | 10/2011 |
| WO | 2012-149278 | 11/2012 |
| WO | 2012-149287 | 11/2012 |

OTHER PUBLICATIONS

Heijl, Anders et al, Reduction of Intraocular Pressure and Glaucoma Progression: Results From the Early Manifest Glaucoma Trial, Arch Ophthalmol, 2002, 1268-1279, 120.

Kass, Michael et al, The Ocular Hypertension Treatment Study: A Randomized Trial Determines That Topical Ocular Hypotensive Medication Delays or Prevents the Onset of Primary Open-Angle Glaucoma, Arch. Ophthalmol., 2002, 701-713, 120.

Kumar, Janoria et al, Novel Approaches to Retinal Drug Delivery, Expert Opinion on Drug Delivery, 2007, 371-388, 4.

Laibovitz, Robert, Comparison of the Ocular Hypotensive Lipid AGN 192024 With Timolol, Arch Ophthal, 2001, 994, 119.

Maruquis, Robert et al., Management of Glaucoma: Focus On Pharmacological Therapy, Drugs & Aging, 2005, 1-21, 22 (1).

Schuster, Victor et al, Synthetic Modification of Prostaglandin F2α Indicates Different Structural Determinants of Binding to the Prostaglandin F Receptor Versus the Prostaglandin Transporter, Molecular Pharmacology, 2000, 1511-1516, 58.

Shaffer, RN, Primary glaucomas. Gonioscopy, ophthalmology and perimetry, Transactions—American Academy of Ophthalmology and Otolaryngology, 1960, 112-27, vol. 64.

U.S. Appl. No. 13/861,688, filed Apr. 12, 2013.

U.S. Appl. No. 13/466,804, filed May 8, 2012.

United States Board of Appeals and Interferences decision on appeal in *Ex parte Huang et al*, Appeal No. 2009-013914, U.S. Appl. No. 10/340,237, mailed Sep. 21, 2010.

United States Board of Patent and Interferences decision on appeal in *Ex parte Huang et al*, Appeal No. 2010-006865, U.S. Appl. No. 10/836,880, mailed Sep. 28, 2010.

United States Board of Patent Appeals and Interferences decision on appeal in *Ex parte Hughes et al*, Appeal No. 2010-004999, U.S. Appl. No. 10/836,911, mailed Oct. 25, 2010.

United States Board of Patent Appeals and Interferences on appeal in *Ex parte Hughes et al*, Appeal No. 2011-003859, U.S. Appl. No. 11/116,698, mailed Aug. 1, 2011.

United States Pharmacopeia, The National Formulary, USP23, 1995, 1790-1798, 18.

U.S. Appl. No. 12/955,630, filed Nov. 29, 2010.

Woodward, David et al, Bimatoprost: a Novel Antiglaucoma Agent, Cardiovascular Drug Reviews, 2004, 103-120, 22(2).

Woodward, David et al, Identification of an antagonist that selectively blocks the activity of prostamides (prostaglandin-ethanolamides) in the feline iris, British Journal of Pharmacology, 2007, 342-352, 150.

Woodward, David et al, Prostamides (Prostaglandin-ethanolamides) and Their Pharmacology, British Journal of Pharmacology, 2008, 410-419, 153.

(56) References Cited

OTHER PUBLICATIONS

Woodward, David et al, The Pharmacology of Bimatoprost (LumiganTM), Surv Ophthalmol, 2001, S337-S345, Suppl 4.

Woodward, et al., "Fixed-Combination and Emerging Glaucoma Therapies", Expert Opinion On Emerging Drugs, 2007, 313-327, 12 (2).

Yu, Ming, et al., Synthesis of Prostaglandin E2 Ethanolamide from Anandamide by Cyclooxygenase-2, The Journal of Biological Chemistry, Aug. 22, 1997, 21181-21186, vol. 272, No. 34, US.

Ford Versypt, A.N., et al., Mathematical modeling of drug delivery from autocatalytically degradable PLGA microspheres—A review, Journal of Controlled Release, Jan. 10, 2013, pp. 29-37, Tables 1, 2, Section 3, vol. 1, Elsevier.

Makadia, Hirenjumar et al, Poly Lactic-co-Glycolic Acid (PLGA) as Biodegradable Controlled Drug Delivery Carrier, Polymers (Basel), 2011, 1377-1397, 3(3).

Siegel, R.A., et al., Overview of Controlled Release Mechanisms, Fundamentals and Applications of Controlled Release Drug Delivery, 2012, 19-43, Chapter 2, Springer US.

\* cited by examiner

Swelling behavior for Bimatoprost Implant Formulations 1 and 2.

Between group comparison of bimatoprost formulations 2, 6, 7 and 8 on IOP reduction in normal Beagle dogs using ANOVA; t = p<0.05. There was a statistically significant difference at 4 months in favor of formulation 8.

Between group comparison of bimatoprost formulations 2, 6, 7 and 8 on pupil size reduction in normal Beagle dogs using ANOVA; t = p<0.05. There was a statistically significant difference at 0.25 and 0.5 months in favor of formulation 2.

PROSTAMIDE-CONTAINING INTRAOCULAR IMPLANTS AND METHODS OF USE THEREOF

CROSS-REFERENCE TO RELATED APPLICATIONS

This application is a continuation of U.S. patent application Ser. No. 14/529,526, filed on Oct. 31, 2014, which claims the benefit of U.S. Provisional Application No. 61/898,241 filed on Oct. 31, 2013, the entire content of both applications are incorporated herein by reference.

BACKGROUND

Described herein are biodegradable intraocular implants that provide for the extended release of bimatoprost in an amount that is effective for treating an ocular condition, particularly glaucoma and ocular hypertension, and conditions associated with glaucoma such as elevated intraocular pressure. The implants, which may be produced by an extrusion process, are sized and configured for placement in the anterior chamber of the eye where the implant can deliver the prostamide directly to the tissues regulating the production and outflow of aqueous humor. Importantly, the intraocular implants described here are designed not only to provide a patient with intraocular pressure-lowering levels of bimatoprost for a sustained period lasting for 2 months or more but are also sized to fit within the anterior chamber angle (also called the iridocorneal angle) of the eye without injuring the corneal endothelium and without obstructing vision. Though developed for the delivery of bimatoprost, implants in accordance with this invention may be useful for the sustained delivery of other prostamides as well. Methods for making and using these implants to treat an ocular condition are described.

Prostamides are potent ocular hypotensive agents useful in the treatment of a number of various ocular hypertensive conditions such as glaucoma, elevated intraocular pressure, and other ocular hypertensive episodes, including post-surgical and post-laser ocular hypertensive episodes (1, 4). They belong to an ever-expanding family of prostaglandin $F_{2\alpha}$ C-1 amides (1-5). The biosynthesis and pharmacology of prostamides has been extensively described (1-3, 9). For example, naturally occurring prostamides, such as prostamide $F_{2\alpha}$, are biosynthesized from anandamide by a pathway exclusively involving COX-2. COX-1 is not involved (1, 2, 15). Other commercially available prostaglandin analogs include travoprost and latanoprost.

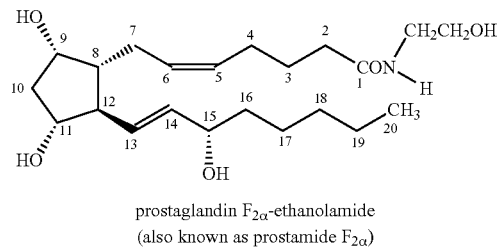

prostaglandin $F_{2\alpha}$-ethanolamide
(also known as prostamide $F_{2\alpha}$)

One prostamide that has found wide-spread use in ocular therapy is bimatoprost. Like other prostamides, bimatoprost exhibits no meaningful interaction with prostaglandin (PG) sensitive receptors (3, 10). Nevertheless, bimatoprost is a potent ocular anti-hypertensive agent and is highly effective for reducing elevated intraocular pressure in patients with open angle glaucoma or ocular hypertension (1, 6-8). Bimatoprost is typically prescribed for use by patients in the form of an ophthalmic solution known by the tradename LUMIGAN®. In the usual course of therapy, Patients apply one drop of LUMIGAN® solution once daily to the surface of the affected eye(s) to reduce elevated intraocular pressure. Bimatoprost is believed to decrease intraocular pressure (IOP) by increasing aqueous humor outflow through the uveoscleral pathway (1, 3).

While highly effective for reducing intraocular pressure, the regular daily instillation of bimatoprost eye drops, nevertheless, requires daily management by the patient. It would be advantageous for some patients to have access to implantable drug delivery systems, such as intraocular implants, that are capable of delivering a therapeutically effective amount of bimatoprost to the eye at a consistent rate for an extended period to thereby reduce intraocular pressure in a hypertensive eye continuously for longer durations such as 2 months or more. A biodegradable intraocular implant, sized and configured for safe comfortable placement in the eye, and properly formulated to deliver a therapeutic amount of bimatoprost to tissues in the eye would effectively eliminate the need for patient compliance, since a patient would no longer need to apply daily eye drops, and by maintaining intraocular pressure at or below the levels typically obtained by topical application continuously for an extended period (such as 2 months or more), an intraocular implant may improve glaucoma therapy and lead to better therapeutic outcomes in some patients. Intraocular implants that include a prostamide component and a biodegradable polymer for the extended release of a prostamide such as bimatoprost, to treat an ocular condition such as glaucoma have been described (Ref 4, for example).

Glaucoma is generally a progressive disease of the eye characterized by progressive optic neuropathy with associated visual field loss. Glaucoma may be further associated with increased intraocular pressure. On the basis of its etiology, glaucoma has been classified as primary or secondary. Primary glaucoma in adults may be either open-angle glaucoma or acute or chronic angle-closure glaucoma. Secondary glaucoma results from pre-existing ocular diseases such as uveitis, intraocular tumor or an enlarged cataract.

The underlying causes of primary glaucoma are not yet known. Risk factors include high or elevated intraocular pressure, advanced age, and family history. Increased or elevated intraocular pressure is due to the obstruction of aqueous humor outflow. In primary open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may obstruct movement of aqueous humor through the pupil leading to elevated intraocular pressure. Other common causes are intraocular tumors, enlarged cataracts, central retinal vein occlusion, trauma to the eye, operative procedures and intraocular hemorrhage. Considering all types together, glaucoma occurs in about 2% of all persons over the age of 40 and may be asymptomatic for years before progressing to noticeable peripheral visual loss followed by central vision loss.

Glaucoma can be considered to be potentially both an anterior and posterior ocular condition because a clinical goal of glaucoma treatment can be not only to reduce elevated intraocular pressure because of obstructed aqueous humor outflow from the anterior chamber, but to also prevent the loss of or reduce the occurrence of loss of vision due to damage to or loss of retinal cells or optic nerve cells (i.e., ganglion cells) in the posterior of the eye (i.e. neuroprotection). Clinical trials have shown that reducing IOP can help retard the progression of glaucoma and consistent IOP reduction is associated with reduced risks of developing and progressing optic nerve damage (11-13).

Patient non-adherence to topical therapy is one of the major challenges to preventing vision loss due to glaucoma. Patients that take no medication are at the highest risk of vision loss from glaucoma; however, patients that intermittently take their medications are also at risk since IOP fluctuation has also been identified as possible risk factor for progression in some patients (14).

Accordingly, sustained-release drug delivery systems, such as biodegradable intraocular implants, that can continuously deliver a therapeutically effective amount of an anti-hypertensive drug such as bimatoprost directly into the anterior chamber of the eye may help reduce patient dependence on topical ocular anti-hypertensives or other antiglaucoma medications to control intraocular pressure and manage symptoms associated with glaucoma.

The present invention provides for such drug delivery systems and offers additional improvements relative to some existing biodegradable intraocular implants. We have discovered a biodegradable implant formulation that swells less and biodegrades faster than some comparable intraocular implants, yet releases a therapeutically effective amount of bimatoprost at a nearly linear or constant rate for a sustained period (e.g., about 60 days), thereby providing patients with long-lasting relief from ocular hypertension and possibly protecting patients from some of the adverse effects caused by high or elevated intraocular pressure.

Such attributes are particularly valuable for implants placed in the anterior chamber of the eye (the fluid-filled space inside the eye between the iris and the innermost corneal surface, the corneal endothelium). Because most anterior chamber implants are more dense than aqueous humor, they tend to settle inferiorly into the angle of the anterior chamber (the junction between the front surface of the iris and the back surface of the cornea; also called the iridocorneal angle) after injection into the anterior chamber, where they may contact and possibly injure the corneal endothelium. Small, low-swell, rapidly degraded implants (i.e. implants that swell to less than 3 times (<3×) the initial size when placed in the anterior chamber), such as the ones we describe here, may reduce the risk of a patient developing corneal edema due to mechanical irritation of the corneal endothelium. In contrast, implants that swell greater than 3 fold (>3×) the initial size when placed in the anterior chamber have a higher risk of corneal endothelial cell touch and formation of corneal edema. Corneal edema can lead to cloudiness of normally transparent cornea and may result in vision loss if it extends to the central cornea. Furthermore, a small, low-swell implant that stays at a maximum swell for a shorter period before decreasing in size may enable physicians to safely administer the implant to a larger population of patients, including those with small or narrow anterior chamber angles. Rapid biodegradation of an implant after its drug load has been delivered means that a patient can receive one or more additional implants as needed as part of their continued therapy without having to worry about residual implants compromising their vision or comfort.

All such considerations, including the optimal size of the implant (e.g., length, diameter or width, and total mass) have been taken into account here in the development of the presently described implants.

REFERENCES CITED

1. Woodward et al. (2001) "The pharmacology of Bimatoprost (Lumigan®)" *Survey of Ophthalmology* Vol. 45, Supplement 4, pp. S337-S345.
2. Woodward et al. (2008) "Prostamides (prostaglandin ethanolamides) and their pharmacology" *British J. Pharmacology* 153:410-419.
3. Woodward et al. (2004) "Bimatoprost: A novel antiglaucoma agent" *Cardiovascular Drug Reviews* 22 (2): 103-120.
4. U.S. Pat. No. 7,799,336, which is herein incorporated by reference.
5. U.S. Pat. No. 6,395,787, which is herein incorporated by reference.
6. Coleman et al. (2003) "A 3-Month Randomized Controlled Trial of Bimatoprost (LUMIGAN®) versus Combined Timolol/Dorzolamide (Cosopt®) in Patients with Glaucoma or Ocular Hypertension" *Ophthalmology* 110 (12): 2362-8.
7. Laibovitz et al. (2001) "Comparison of the ocular hypotensive lipid AGN 192024 with timolol. Dosing, efficacy and safety evaluation of a novel compound for glaucoma management" *Arch Ophthalmol* 119:994-1000.
8. Cantor (2008) "An update on bimatoprost in glaucoma therapy" *Expert Opin. Pharmacother.* 3 (12):1753-1762.
9. Brubaker et al. (2001) "Effects of AGN 19024, a new ocular hypotensive agent, on aqueous dynamics" Am. J. Ophthalmol. 131:19-24.
10. Schuster et al. (2000) "Synthetic modification of prostaglandin $F_{2\alpha}$ indicates different structural determinants for binding to the prostaglandin F receptor versus the prostaglandin transporter" *Mol. Pharmacology* 58:1511-1516.
11. Collaborative Normal-tension glaucoma study group. The effectiveness of intraocular pressure reduction in the treatment of normal-tension glaucoma. *Am. J. Ophthalmology* 1998; 126:498-505.
12. Heijl et al. (2002) "Reduction of intraocular pressure and glaucoma progression: results from the early manifest glaucoma trial." *Arch. Ophthalmol.* 120:1268-1279.
13. Kass et al. (2002) "The ocular hypertension treatment study: a randomized trial determines that topical ocular hypotensive medication delays or prevents the onset of primary open-angle glaucoma" *Arch. Ophthalmol* 120: 701-713.
14. Caprioli et al. (2008) "Intraocular pressure fluctuation" *Ophthalmology* 115 (7):1123-1129.
15. Yu et al. (1997) "Synthesis of prostaglandin $E_2$ ethanolamide from anandamide by cyclooxygenase-2" *J. Biol. Chem.* 272 (34):21181-21186.

SUMMARY

The present disclosure provides for a bimatoprost-containing biodegradable intraocular implant for reducing intraocular pressure (IOP) in an eye for at least 2 months. The implant may be effective for maintaining intraocular pressure in an eye at a reduced level (relative to the intraocular pressure in the eye before receiving the implant) for 4 months, for 4-6 months, or for 6-12 months or longer than 12 months after placement in the eye. The percent relative reduction in IOP in an eye after receiving the implant may vary, depending on the size of the implant (and therefore the drug load) and on the patient, but may be from 10-20%, 20-30%, or 10-50% below baseline IOP (the intraocular pressure in the eye before receiving the implant) and may, in some instances, remain at 20-30% below baseline IOP for at least 2 months, 2-3 months, for 4 months or longer, and in some instances for 6-12 months or longer after implantation of a single implant.

The implant may be placed in an ocular region of an eye of a patient to reduce intraocular pressure in the eye and thereby to treat ocular hypertension and ocular conditions associated with elevated intraocular pressure, including glaucoma. The bimatoprost-containing implant described here is specifically sized and formulated for placement in the anterior chamber of the eye, but may be adopted for use in the vitreous body of the eye (by intravitreal injection) if desired and as may be necessary in some patients with a small or narrow anterior chamber angle or in patients with angle-closure glaucoma. Anterior chamber angle widths may be graded according to the Shaffer System (Shaffer R N. (1960) "Primary glaucomas. Gonioscopy, ophthalmoscopy, and perimetry" *Trans Am Acad Ophthalmol Otolaryngol.* 64:112-127). Shaffer Grade 1 and Grade 2 angles may be considered narrow. It may be preferable to treat patients that have either a Shaffer Grade 1 or Grade 2 angle by placing the implant in the vitreous body of the eye rather than the anterior chamber to reduce the chance of corneal toxicity. Patients with open angles, such as patients with Shaffer Grade 3 and 4 angles, may be candidates for either an intracameral implant or an intravitreal implant.

While initially developed for the sustained delivery of bimatoprost, the intraocular implants, or drug delivery systems, described here may be useful for the delivery of other prostamides as well, including, but not limited to, the compounds having Formula I, set forth below.

In general, an intraocular implant in accordance with this disclosure comprises or consists of bimatoprost as the active agent, a biodegradable polymer matrix, and optionally a polyethylene glycol. The bimatoprost (or other prostamide) may comprise from 5% to 90% by weight of the implant, or from 5% to 30% by weight of the implant, or from 18-22% by weight of the implant, but is preferably 20% by weight of the implant. The biodegradable polymer matrix will generally comprise a mixture of at least three different biodegradable polymers independently selected from the group consisting of poly(D,L-lactide) (PLA) polymers and poly(D,L-lactide-co-glycolide) (PLGA) polymers. For example, the biodegradable polymer matrix may comprise or consist of first, second, and third biodegradable polymers that differ one from the other by their repeating unit, inherent viscosity, or end-group, or any combination thereof. In some instances, the biodegradable polymer matrix according to the present disclosure may comprise first, second, third, and fourth biodegradable polymers independently selected from the group consisting of poly(D,L-lactide) (PLA) polymers and poly(D,L-lactide-co-glycolide) (PLGA) polymers, wherein the first, second, third, and fourth polymers differ one from the other by their repeating unit, inherent viscosity, or end-group, or any combination thereof. Depending on the chain terminating agent used during the synthesis of the polymer, a PLA or PLGA polymer may have a free carboxylic acid end group or alkyl ester end group, and may be referred to herein as an acid-end or ester-end (or ester-capped) PLA or PLGA polymer, respectively.

In one embodiment, the biodegradable polymer matrix comprises or consists of first, second, and third biodegradable polymers, wherein the first biodegradable polymer is an ester-end poly(D,L-lactide) polymer having an inherent viscosity of 0.25-0.35 dl/g, the second polymer is an acid-end poly(D,L-lactide) polymer having an inherent viscosity of 0.16-0.24 dl/g, and the third polymer is a ester-end poly(D,L-lactide-co-glycolide) polymer having a D,L-lactide:glycolide molar ratio of from 73:27 to 77:23, or about 75:25, and an inherent viscosity of 0.16-0.24 dl/g, where the inherent viscosity of each polymer is determined for a 0.1% w/v solution of the polymer in chloroform at 25° C.

The prostamide contained by the implant may be uniformly or non-uniformly distributed throughout the biodegradable polymer matrix. The prostamide may be dispersed within the biodegradable polymer matrix.

As stated above, the implant may further comprise polyethylene glycol. The polyethylene glycol contained by the implant may have an average molecular weight of from 3000 to 20,000 g/mol. In one embodiment the implant contains polyethylene glycol 3350 (PEG 3350). The polyethylene glycol will generally be associated with the biodegradable polymer matrix. For example, the polyethylene glycol may be dispersed within the biodegradable polymer matrix.

Prostamide-containing implants in accordance with this disclosure are formulated to i) minimize the swelling of the implant in the liquid filled interior of the eye, ii) hasten implant degradation following depletion of the drug payload, and iii) to release drug at a substantially constant (or near linear) rate for an extended period, which may be for 2 months or more following placement in the eye. Such implants are considered to be well suited for long term reduction of intraocular pressure in a hypertensive eye. As previously discussed, the implant is sized to fit in the anterior chamber angle (also called the iridocorneal angle) of the eye (particularly a human eye) without contacting or without injuring the corneal endothelium. Minimizing contact between the implant and the corneal endothelium may lower or eliminate the possibility of the patient developing corneal edema, a condition that can impair vision and possibly lead to vision loss.

In this regard, one embodiment is a biodegradable intraocular implant for reducing intraocular pressure or ocular hypertension in a patient, the implant comprising a biodegradable polymer matrix and a prostamide as the active agent associated with the biodegradable polymer matrix, the biodegradable polymer matrix comprising or consisting of
  a) R203S, which is an ester end poly(D,L-lactide) having an inherent viscosity of 0.25-0.35 dl/g;
  b) R202H, which is an acid end poly(D,L-lactide) having an inherent viscosity of 0.16-0.24 dl/g;
  c) RG752S, which is an ester end poly(D,L-lactide-co-glycolide) having a D,L-lactide:glycolide molar ratio of about 75:25 and an inherent viscosity of 0.16-0.24 dl/g; and
  d) polyethylene glycol 3350;
wherein the prostamide comprises 20% of the implant by weight, the ester end poly(D,L-lactide) comprises 20% of the implant by weight, the acid end poly(D,L-lactide) comprises 15% of the implant by weight, the ester end poly(D,L-lactide-co-glycolide) comprises 40% of the implant by weight, and wherein the polyethylene glycol (PEG) 3350 comprises 5% of the implant by weight, wherein the inherent viscosities for each of the poly(D,L-lactide) and poly(D,L-lactide-co-glycolide) polymers are measured for a 0.1% solution of the polymer in chloroform at 25° C.

In some embodiments, the prostamide is a compound having Formula I. In one embodiment the prostamide is bimatoprost.

Examples of intraocular implants for use in a method of treating an ocular condition in accordance with this disclosure include those set forth in Tables 1 and 2, below. For example an intraocular implant for reducing intraocular pressure and ocular hypertension in a patient may comprise 20% by weight bimatoprost, 15% by weight R203S, 20% by weight RG858S, 40% by weight RG752S, and 5% by weight polyethylene glycol 3350. RG858S is an ester end poly(D,L-lactide-co-glycolide) having an inherent viscosity of 1.3-1.7 dl/g and a D,L-lactide to glycolide ratio of 83:17 to 87:13, or about 85:15.

Another embodiment is a biodegradable intraocular implant for treating an ocular condition in an eye of a patient, the implant comprising 18-22% by weight (w/w) bimatoprost, 18-22% by weight R203S, 13.5-16.5% by weight R202H, 36-44% by weight RG752S, and 3.5-6.5% by weight polyethylene glycol.

An additional embodiment is a biodegradable intraocular implant for treating an ocular condition in an eye of a patient, the implant comprising 20% by weight (w/w) bimatoprost, 20% by weight R203S, 15% by weight R202H, 40% by weight RG752S, and 5% by weight polyethylene glycol.

Another embodiment is a biodegradable intraocular implant for treating an ocular condition in an eye of a patient, the implant comprising 20% by weight (w/w) bimatoprost, 15% by weight RG858S, 35% by weight RG752S, 15% by weight RG755S, and 15% by weight RG502S. RG755S is a poly(D,L-lactide-co-glycolide) having an ester end group, an inherent viscosity of about 0.50-0.70 dl/g (as measured for a 0.1% solution in chloroform at 25° C.), and a D,L-lactide:glycolide molar ratio of 73:27 to 77:23, or about 75:25. RG502S is a poly(D,L-lactide-co-glycolide) having an ester end group, an inherent viscosity of 0.16-0.24 dl/g (as measured for a 0.1% solution in chloroform at 25° C.), and a D,L-lactide:glycolide ratio of 48:52 to 52:48, or about 50:50.

Another embodiment is a biodegradable intraocular implant for treating an ocular condition in an eye of a patient, the implant comprising 20% by weight (w/w) bimatoprost, 30% by weight RG858S, 40% by weight RG752S, 5% by weight RG502, and 5% by weight RG502H. RG502H is a poly(D,L-lactide-co-glycolide) having an acid end group, an inherent viscosity of 0.16-0.24 dl/g (as measured for a 0.1% solution in chloroform at 25° C.), and a D,L-lactide:glycolide ratio of about 50:50 (such as for example RG502H).

Another embodiment is a biodegradable intraocular implant comprising 20% by weight (w/w) bimatoprost, 20% by weight RG752S, 50% by weight RG755S, 5% by weight RG502, and 5% by weight RG502H.

Another embodiment is a biodegradable intraocular implant comprising 20% by weight (w/w) bimatoprost, 25% by weight RG752S, 50% by weight RG755S, and 5% by weight RG502.

Another embodiment is a biodegradable intraocular implant comprising 20% by weight (w/w) bimatoprost, 30% by weight RG752S, 20% by weight RG502, and 30% by weight RG858S.

As set forth above, an implant formulation according to this disclosure may contain bimatoprost or other prostamide. In some embodiments, the prostamide contained by the implant comprises a compound having the Formula (I)

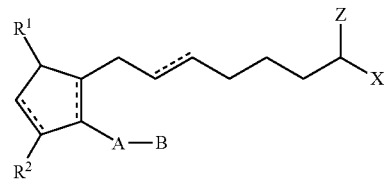

wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or alkylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is —N($R^4$)$_2$ wherein $R^4$ is independently selected from the group consisting of hydrogen and a lower alkyl radical having from one to six carbon atoms; Z is =O; one of $R^1$ and $R^2$ is =O, —OH or a —O(CO)$R^6$ group, and the other one is —OH or —O(CO)$R^6$, or $R^1$ is =O and $R^2$ is H, wherein $R^6$ is a saturated or unsaturated acyclic hydrocarbon group having from 1 to about 20 carbon atoms, or —(CH$_2$)$_m$ $R^7$ wherein m is 0 or an integer of from 1 to 10, and $R^7$ is cycloalkyl radical, having from three to seven carbon atoms, or a hydrocarbyl aryl or heteroaryl radical, as defined above.

In a more specific embodiment the prostamide contained by the implant is bimatoprost, which has the following chemical structure:

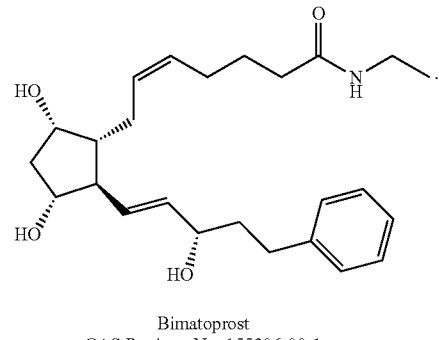

Bimatoprost
CAS Registry No. 155206-00-1

Other examples of prostamides (prostaglandin F$_{2\alpha}$ amides) may include, but are not limited to, the prostaglandin F$_{2\alpha}$ amides described in Woodward et al. (2008) "Prostamides (prostaglandin ethanolamides) and their pharmacology" *British J. Pharmacology* 153:410-419; and Schuster et al. (2000) "Synthetic modification of prostaglandin F$_{2\alpha}$ indicates different structural determinants for binding to the prostaglandin F receptor versus the prostaglandin transporter" *Molecular Pharmacology* 58:1511-1516; and the prostaglandin F$_{2\alpha}$ amides described in U.S. Pat. Nos. 5,688,819 and 5,834,498, which are herein incorporated by reference.

The biodegradable polymer matrix of an implant according to this disclosure may release a prostamide at a rate to sustain release of a therapeutically effective amount of the prostamide from the implant for a period of two months from a time in which the implant is placed in an ocular region of an eye. In some instances, the implant may be effective for reducing intraocular pressure in an eye for at least 4 months, for 4-6 months or longer, for 6-12 months, or for 12 to 24 months after placement of the implant in an eye. The implant is designed specifically for placement in the anterior chamber of the eye, but may be suitable for placement in other ocular regions to treat conditions such as glaucoma and ocular hypertension, or to generally reduce IOP in an eye. Accordingly, an implant according to this disclosure may, for example, be placed in the anterior chamber, posterior chamber, or vitreous body of the eye. In some instances, an implant may be placed in a subconjunctival or subtenon space in the eye.

The polyethylene glycol (PEG) in any of the foregoing embodiments may have an average molecular mass of from 3,000 to 20,000 g/mol. In preferred embodiments the polyethylene glycol in the implant is PEG 3350. For example, in one embodiment the present invention provides for a biodegradable intraocular implant comprising 20% by weight (w/w) bimatoprost, 20% by weight R203S, 15% by weight R202H, 40% by weight RG752S, and 5% by weight polyethylene glycol 3350 (Formulation 2). More generally, the implant can comprise 18-22% by weight (w/w) bimatoprost, 18-22% by weight R203S, 13.5-16.5% by weight R202H, 36-44% by weight RG752S, and 3.5-6.5% by weight polyethylene glycol.

The intraocular implants according to this disclosure may be effective for reducing intraocular pressure in either a normotensive or hypertensive eye for an extended period. In some embodiments of the present methods, a patient may have normal tension glaucoma (NTG), with an intraocular pressure ranging from 11 to 21 mm Hg. Such patients may require even lower eye pressures to reduce the risk of progressive optic nerve damage and visual field loss, and may benefit from the intraocular administration of an implant according to this disclosure. Thus, an implant according to this disclosure may be effective for treating glaucoma in all its forms, including glaucoma characterized by elevated intraocular pressure, as well as low-tension or normal-tension glaucoma, since these patients, too, may potentially benefit from a further reduction in intraocular pressure.

The implant may be effective for reducing intraocular pressure in an eye by 10-20%, 20-30%, and possibly by 30-40% or more (with higher drug release rates), relative to the intraocular pressure (IOP) in the eye before receiving the implant, for 2 months or more, 4 months or more, and potentially 6 months or more, after placement of the implant in the eye. Such implants may further be effective for reducing the risk of developing, delaying the onset of, or slowing the progression of glaucomatous damage in an eye of a patient. Glaucomatous damage in the eye may include damage to the function and/or structure of the optic nerve and ganglion cell death, which can lead to loss of peripheral visual fields and eventually central vision loss leading to total blindness. Elevated IOP presents a major risk factor for glaucomatous field loss.

Accordingly, the presently described implants may be effective for treating a patient suffering from or diagnosed with an ocular condition selected from glaucoma, open angle glaucoma, primary open-angle glaucoma, angle-closure glaucoma (sometimes referred to as closed-angle glaucoma), normal-tension glaucoma, low-tension glaucoma, pseudoexfoliative glaucoma, developmental glaucoma, or pigmentary glaucoma. One or more of the present implants may also be useful for reducing and thereby treating ocular hypertension or elevated intraocular pressure. For example, an implant according to this disclosure may be effective for reducing intraocular pressure in a patient with open-angle glaucoma, angle-closure glaucoma, or ocular hypertension. The patient can be a human or non-human mammal. The method will generally comprise the step of placing the implant in an ocular of the eye affected by the ocular condition.

Because of their ability to release a therapeutically effective amount of bimatoprost for an extended period (e.g., 60 days or longer), implants in accordance with this disclosure are expected to be capable of reducing intraocular pressure in a patient for long periods (e.g., for 4 months or more) without the need for frequent intraocular injections or regular instillation of eye drops to the ocular surface as may be necessary with topical therapy. Accordingly, in some forms of the present invention, the implants described here are used as monotherapy (i.e. used alone to control the IOP without the use of adjunctive antihypertensive eye drops) to reduce intraocular pressure in a patient and thereby treat an ocular condition as described herein. Nevertheless, an implant in accordance with this disclosure can, if desired, be used in dual therapy in conjunction with the same or different therapeutic agent that is applied topically.

Thus, one embodiment is a method for treating an ocular condition in a patient, the method comprising placing a biodegradable intraocular implant according to this disclosure in the eye(s) affected by the ocular condition, thereby treating the ocular condition in the eye(s). The implant is preferably placed in the anterior chamber of the eye, but may be placed in the posterior chamber (i.e. the region of the eye immediately behind the iris in the ciliary sulcus) or vitreous body of the eye. Placement in the vitreous body (intravitreal placement) may be preferred in patients with narrow anterior chamber angles such as those patients with Shaffer Grade 1 or 2 angles, wherein the iris is closely approximated to the trabecular meshwork nearing the threshold to start obstructing aqueous humor outflow resulting in an elevation of the intraocular pressure. Shaffer Grade 1 and 2 patients should receive intravitreal implants rather than an intracameral implant to reduce the chance of corneal toxicity. A Shaffer grade of 0 is considered to be a closed angle, wherein the iris completely occludes the trabecular meshwork, leading to high intraocular pressure and the potential for optic nerve damage and blindness. Patients that can fit or tolerate maximal intracameral implant diameter swells of about 400 µm or greater will generally have Shaffer Grade 3 to 4 (wide open) angles, whereas angles that are Shaffer Grade 1 and 2 may only accommodate implants with a maximum diameter swell of about 200 µm to less than about 400 µm.

The implant will preferably provide a therapeutically effective dose of the prostamide to the eye(s) for at least two months after placement in the eye, and will reduce the ocular condition, or at least one sign or symptom, or risk factor associated with the ocular condition, for at least 1 month, or for at least 2, or 4 months following placement of the implant in the anterior chamber of the eye. If desired, more than one implant can be placed in the eye. For example, two implants may be placed in the anterior chamber or vitreous body of the eye to deliver a larger dose of the prostamide. For example, in one method an eye may be dosed with 20 µg of bimatoprost, by placing two 50-µg implants (each containing 20% bimatoprost by weight) in the anterior chamber of the eye simultaneously rather than using a single 100-μg implant. Using two smaller implants may possibly improve the tolerability of the implants in the eye and further reduce the risk of an implant contacting the corneal endothelium, thereby lessening or altogether eliminating the chance that the eye will experience a loss of corneal endothelial cell density and onset of corneal edema.

One example of a prostamide-containing intraocular implant according to this disclosure is an extruded intraocular implant comprising Formulation 2, as set forth in Table 1, below. In some embodiments, an implant comprises any of Formulations 2-8 and is sized for placement in the anterior chamber of the eye. The anterior chamber implant will preferably fit within the anterior chamber angle without contacting or rubbing against the corneal endothelium after placement in the eye.

As mentioned previously, examples of an ocular condition according to this method include elevated intraocular pressure, ocular hypertension, and glaucoma, including, for example open angle glaucoma or angle-closure glaucoma. While various prostamides may be delivered with the present method, the implants described here are especially useful for the delivery of (and will therefore contain as the sole active agent) bimatoprost.

One embodiment is a method for reducing ocular pressure in an eye of a mammal, the method comprising placing a biodegradable intraocular implant according to this disclosure in an eye of the mammal, whereby the implant provides a prostamide to the eye in an amount effective for reducing ocular pressure in the eye. In some forms of this method the mammal is a human patient that has elevated intraocular pressure, ocular hypertension, or glaucoma, and the implant is placed in the anterior chamber of the affected eye(s) of the patient. The implant may be effective for reducing intraocular pressure in the eye for at least two months after placement in the anterior chamber of the eye. In some instances, the implant may reduce intraocular pressure in the eye for 6-12 months or greater than 12 months after placement of the implant in the eye. In one embodiment the prostamide provided by the implant is bimatoprost. Preferably, the implant is sized and formulated for placement in the anterior chamber of the eye and does not contact and/or does not injure the corneal endothelium after placement in the anterior chamber of an eye, such as for example a human eye. Eliminating contact between the implant and the corneal endothelium may reduce the risk of corneal endothelial cell density reduction and onset of corneal edema in the eye.

The present disclosure also provides for a method for reducing or lowering intraocular pressure in a patient, the method comprising placing a biodegradable intraocular implant in an eye of the patient, thereby reducing intraocular pressure in the eye for an extended period such as, for example, for at least one month, two months, or for at least four months. In some instances, the patient may have open-angle glaucoma, or more specifically primary open-angle glaucoma, and/or ocular hypertension. The implant used in the method can be any of the prostamide-containing implants described herein. In a preferred embodiment, the method comprises placing an extruded intraocular implant comprising Formulation 2 in an eye of the patient. The implant can be placed in the anterior chamber, vitreous body, or posterior chamber of the eye, for example. In some instances, the implant may be specifically placed in the anterior chamber angle (iridocorneal angle) of the eye, and even more specifically in the inferior iridocorneal angle of the eye.

Examples of medically beneficial effects that may be produced by the present treatment methods may include but are not limited to a reduction in intraocular pressure. In some instances, the method may possibly retard or inhibit the progression of glaucoma or glaucomatous damage in the eye, and/or retard or delay visual field loss in a patient, as compared to patients that do not receive an implant.

The implants of the present invention may be inserted into the eye by a variety of methods using a suitable ocular implant delivery device. One example may include the device disclosed in U.S. Pat. No. 6,899,717, the relevant disclosure of which is herein incorporated by reference.

In one embodiment, the implant is placed in the eye(s) using an intraocular delivery apparatus, the apparatus comprising an elongate housing and a cannula extending longitudinally from the housing, the cannula having a proximal end and a distal sharp end and having a lumen extending therethrough, the lumen having an inner diameter sufficient to receive the implant and permit passage of the implant through the lumen and into the eye of the patient. The apparatus may further comprise a push rod or plunger operably connected with a user-actuated linkage for ejecting the implant through the lumen into the eye.

Another embodiment of the present invention is an apparatus for delivering a biodegradable intraocular implant into the eye of a patient, the apparatus comprising an intraocular implant according to any of those described herein, an elongate housing and a cannula extending longitudinally from the housing, the cannula having a proximal end, a distal sharp end, and a lumen extending therethrough, the lumen having an inner diameter sufficient to receive the intraocular implant and permit translation of the implant through the lumen and into the eye of the patient. The cannula may be a 25 gauge, 26 gauge, 27 gauge, 28 gauge, 29 gauge, or 30 gauge needle, or may otherwise be described as having inner and outer diameters equivalent to those of a 25 gauge, 26 gauge, 27 gauge, 28 gauge, 29 gauge, or 30 gauge needle. The needle, in addition, may be a thin-wall or ultra-thin-wall needle.

The present disclosure also provides for methods of making a biodegradable intraocular prostamide-containing implant that will release a therapeutically effective amount of a prostamide in an eye for at least 60 days (two months). The method generally comprises combining a prostamide, at least three biodegradable polymers, and optionally a polyethylene glycol to form a combination of components, blending the combination to form a blended mixture, heating the blended mixture, then extruding the heated mixture to form a filament, and then cutting the filament to form an implant suitable for placement in an ocular region of an eye of a patient. For example, the implant may be cut to a length suitable (sized) for placement in the anterior chamber or vitreous body of the eye of the patient. Each of the components may be combined as dry powders or as dry solids. The blending step may therefore comprise dry powder blending. The at least three biodegradable polymers may be selected from the group consisting of poly(D,L-lactide) (PLA) polymers and poly(D,L-lactide-co-glycolide) (PLGA) polymers. For example, the at least three biodegradable polymers may consist of first, second, and third biodegradable polymers that differ one from the other by their repeating unit, inherent viscosity, and/or end-group. In some instances, the at least three biodegradable polymers may consist of first, second, third, and fourth biodegradable polymers that differ one from the other. The first, second, third, and, optionally fourth biodegradable polymers may be selected from acid-end and ester-end PLA and PLGA polymers. For example, the first, second, third, and optionally fourth biodegradable polymers used to make the implants according to the method described above may be selected from the group consisting of RESOMER® Biodegradable Polymers R203S, R202H, RG502, RG502H, RG752S, RG755S, and RG858S, wherein RG502 is a poly(D,L-lactide-co-glycolide) having an ester end group and an inherent viscosity of 0.16-0.24 dl/g and a D,L-lactide:glycolide ratio of about 50:50, RG502H is a poly(D,L-lactide-co-glycolide) having an acid end group and an inherent viscosity of 0.16-0.24 dl/g, and a D,L-lactide:glycolide ratio of about 50:50, and RG755S is an ester end poly(D,L-lactide-co-glycolide) having an inherent viscosity of 0.50-0.70 dl/g and a D,L-lactide:glycolide ratio of about 75:25. In one embodiment the polyethylene glycol is polyethylene glycol 3350 (PEG 3350).

Thus, one embodiment is a method for making a biodegradable intraocular implant comprising mixing a prostamide with a) an ester end poly(D,L-lactide) having an inherent viscosity of 0.25-0.35 dl/g, b) an acid end poly(D,L-lactide) having an inherent viscosity of 0.16-0.24 dl/g, and c) an ester end poly(D,L-lactide-co-glycolide) having an inherent viscosity of 0.16-0.24 dl/g and a D,L-lactide to glycolide molar ratio of about 75:25, and with polyethylene glycol 3350, extruding the mixture to form a filament, followed by cutting the filament to length suitable for placement in the anterior chamber or vitreous body of an eye to thereby form an intraocular implant, wherein the prostamide comprises about 20% of the implant by weight, the ester end poly(D,L-lactide) comprises about 20% of the implant by weight, the acid end poly(D,L-lactide) comprises about 15% of the implant by weight, the ester end poly(D,L-lactide-co-glycolide) comprises about 40% of the implant by weight, and the polyethylene glycol 3350 comprises about 5% of the implant by weight.

A further embodiment is an intraocular biodegradable implant made by any of the methods described above.

Unless otherwise specified the inherent viscosity for the PLA and PLGA polymers set forth herein is measured for a 0.1% solution of the polymer in chloroform at 25° C.

DETAILED DESCRIPTION

Definitions

Figure 1:
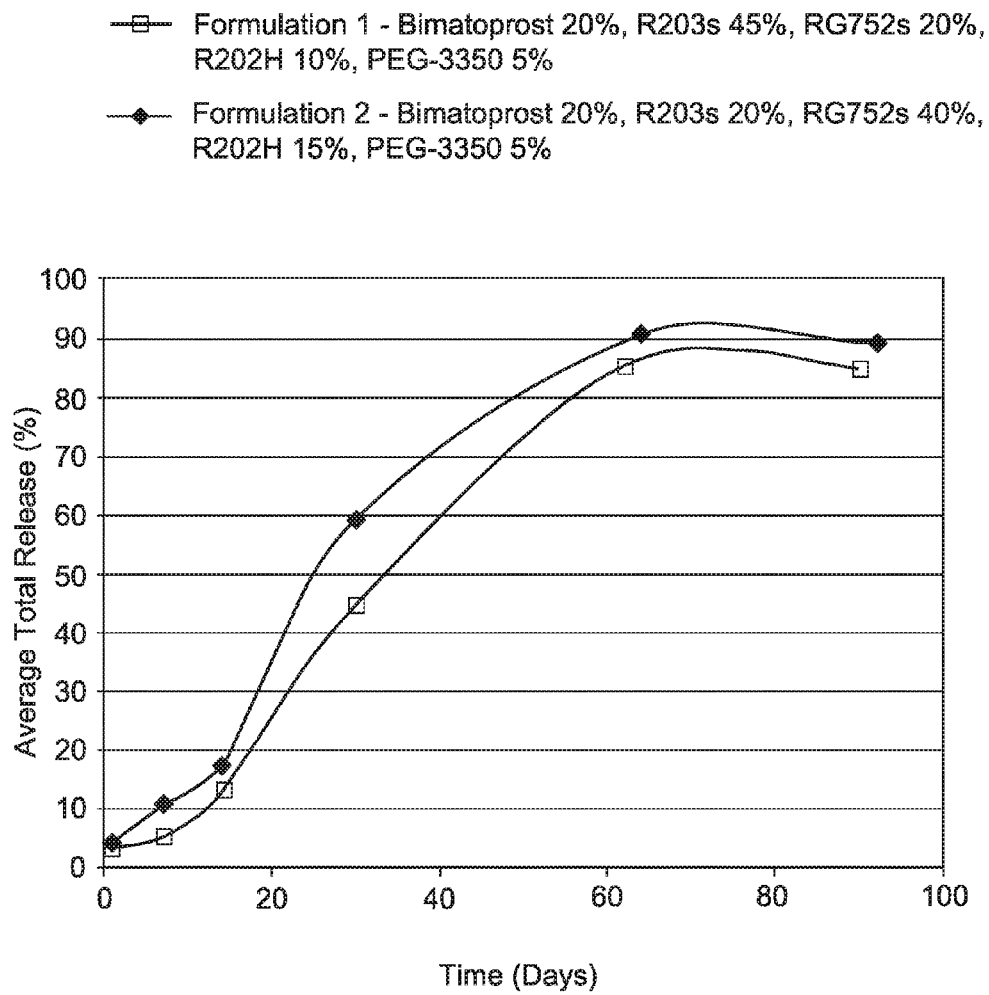
FIG. 1 shows the in vitro cumulative release of bimatoprost (as a percent of the total amount of bimatoprost loaded in the implant) over time from an extruded implant having either Formulation 1 or Formulation 2 (see Table 1), following placement of the implant in 0.01 M phosphate buffered saline (pH 7.4) at 37° C. Each data point represents the average of 3 to 4 replicate samples. The implants in this study each weighed about 50 μg and had a length of about 1.05 mm and a diameter of about 200 μm.

For the purposes of this description, we use the following terms as defined in this section, unless the context of the word indicates a different meaning.

The Terms

As used herein, an "intraocular implant" and "intraocular drug delivery system" refers to a device or element that is structured, sized, or otherwise configured to be placed in an eye and that is capable of delivering a therapeutic level of a drug to the eye. Intraocular implants and drug delivery systems in accordance with the present disclosure are generally biocompatible with physiological conditions of an eye and do not cause adverse side effects or immunological reaction. The implants are preferably completely biodegradable. Intraocular implants may be placed in an eye without disrupting vision of the eye. Non-limiting examples include extruded filaments or rods comprising a biodegradable polymer matrix and an active agent, such as bimatoprost, associated with the polymer matrix, and having a diameter and cut to a length suitable for placement in an ocular region of the eye, such as the anterior chamber.

An "intracameral implant" is an intraocular implant that is structured, sized, or otherwise configured to be placed in the anterior chamber of an eye. The anterior chamber of the eye refers to the fluid-filled space inside the eye between the iris and the innermost corneal surface (corneal endothelium). An intracameral implant will preferably fit into the anterior chamber angle, the junction of the front surface of the iris and back surface of the cornea, without contacting the corneal endothelium and thereby without causing corneal trauma, inflammation, or edema, or iris chaffing.

An "intravitreal" implant is an intraocular implant that is sized for placement in the vitreous body of the eye.

As used herein, "associated with the biodegradable polymer matrix" can mean any one or more of mixed with, dispersed within, coupled to, covering, or surrounding. Usually, the prostamide is non-covalently associated with the polymer matrix and is dispersed within and/or throughout the matrix.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of ocular regions in the eye include the anterior chamber, the posterior chamber, the vitreous cavity, the vitreous body, the choroid, the suprachoroidal space, the conjunctiva, the subconjunctival space, the sub-tenon space, the episcleral space, the intracorneal space, the epicorneal space, the sclera, the pars plana, surgically-induced avascular regions, the macula, and the retina.

As used herein, an "ocular condition" is a disease, ailment or medical condition which affects or involves the eye or one of the parts or regions of the eye. An ocular condition may be classified as an anterior or posterior ocular condition. Broadly speaking the eye includes the eyeball and the tissues and fluids which constitute the eyeball, the periocular muscles (such as the oblique and rectus muscles) and the portion of the optic nerve which is within or adjacent to the eyeball. Examples of an ocular condition within the scope of this disclosure include elevated intraocular pressure, ocular hypertension, and glaucoma. Glaucoma in a patient may be further classified as open-angle glaucoma or angle-closure glaucoma. A patient may be specifically diagnosed with primary open-angle glaucoma.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the ciliary body, the posterior chamber, the lens or the lens capsule and blood vessels and nerve which vascularize or innervate an anterior ocular region or site. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site. Glaucoma can also be considered a posterior ocular condition because the therapeutic goal is to prevent the loss of or reduce the occurrence of loss of vision due to damage to or loss of retinal cells or optic nerve cells (i.e. neuroprotection).

Intraocular pressure refers to the fluid pressure in the eye and is determined by the difference in the rate of aqueous humor secretion and outflow. Approximately 90% of the aqueous humor secreted exits through the trabecular meshwork in the anterior chamber. Resistance to outflow can lead to elevated intraocular pressure. Some populations or patient groups with normal tension (i.e., normotensive) glaucoma may have an IOP of from about 11 to 21 mm Hg. Some patient groups or patients with elevated intraocular pressure or ocular hypertension may have an IOP of greater than 20 or 21 mm Hg, as measured with a tonometer. Implants of the present disclosure are expected to be capable of reducing intraocular pressure in both normotensive and hypertensive glaucoma patients.

The term "biodegradable polymer" and "biodegradable intraocular implant" refers to a polymer or intraocular implant that degrade in vivo, and wherein erosion of the polymer or implant over time occurs concurrent with or subsequent to release of the therapeutic agent. The terms "biodegradable" and "bioerodible" are equivalent and are used interchangeably herein. A biodegradable polymer may be a homopolymer, a copolymer, or a polymer comprising more than two different polymeric units. Examples of biodegradable polymers within the scope of this disclosure are poly(D,L-lactide) polymers and poly(D,L-lactide-co-glycolide) copolymers.

The terms "treat," "treating," or "treatment" as used herein, refers to reduction or resolution or prevention of an ocular condition, ocular injury or damage, or to promote healing of injured or damaged ocular tissue. A treatment may be effective to reduce at least one sign or symptom of the ocular condition or risk factor associated with an ocular condition.

The term "therapeutically effective amount" as used herein, refers to the level or amount of agent needed to treat an ocular condition, or reduce or prevent ocular injury or damage without causing significant negative or adverse side effects to the eye or a region of the eye.

"Active agent," "drug," "therapeutic agent," "therapeutically active agent," and "pharmaceutically active agent" refer to the chemical compound that produces a therapeutic effect in the patient to which it is administered and that can be used to treat the ocular condition in the patient. One example of a therapeutically active agent and therapeutic agent in the context of the present invention is bimatoprost. In preferred embodiments the therapeutic effect is an intraocular pressure (IOP)-lowering effect, which can be identified by applying the compound to an eye and evaluating whether the intraocular pressure decreases after application.

Unless further specified, a "patient" refers to a human subject or non-human mammal in need of treatment for the ocular condition. For example, a patient may be further classified as a human patient. The term "mammal" includes both human patients and non-human mammals. Non-limiting examples of non-human mammals that may be subjects for any of the presently disclosed methods can include horses, dogs, monkeys, pigs, rabbits, and the like.

The term "biocompatible" and "compatible" means compatible with living tissue or a living system. Biocompatible implants and polymers produce few or no toxic effects, are not injurious, or physiologically reactive with living tissue and do not cause an immunological reaction.

"Cumulative release profile" means the cumulative total percent of an active agent (such as bimatoprost) released from an implant into an ocular region in vivo over time or into a specific release medium in vitro over time.

"Suitable (or configured) or sized for insertion, implantation, or placement in (or into) an ocular region" with regard to an implant, means an implant which has a size (dimensions) such that it can be inserted, implanted, or placed in an eye without causing excessive tissue damage or physically impairing the existing vision of the patient into which the implant is implanted or inserted.

DESCRIPTION

The presently disclosed intraocular implants may be effective in treating an ocular condition in an eye of a patient, including an ocular condition associated with elevated intraocular pressure, and more specifically in reducing at least one sign or symptom of, or risk factor for glaucoma. The method generally comprises placing a biodegradable intraocular implant in an ocular region of the eye(s) of the patient affected by the ocular condition. One embodiment is a method for reducing intraocular pressure in a patient suffering from elevated intraocular pressure, ocular hypertension, or glaucoma, comprising placing a prostamide-containing biodegradable intraocular implant according to this invention in an eye of the patient to thereby reduce intraocular pressure in the eye. Controlled and sustained administration of a prostamide such as bimatoprost to the eye through the use of one or more of the intraocular prostamide-containing implants described here may improve glaucoma treatment by reducing intraocular pressure in a patient suffering from glaucoma or ocular hypertension for an extended period of time, such as for 4, 5, or 6 months or more following placement of the implant in the eye. Injection of one or two implants of the present disclosure into an eye of a patient may possibly reduce the diurnal fluctuation in intraocular pressure (IOP) in the eye for about two months or longer as compared to the diurnal fluctuation in an eye treated with once daily topical administration of bimatoprost to an eye.

Examples of antioxidant agents include ascorbate, ascorbic acid, alpha-tocopherol, mannitol, reduced glutathione, various carotenoids, cysteine, uric acid, taurine, tyrosine, superoxide dismutase, lutein, zeaxanthin, cryptoxanthin, astaxanthin, lycopene, N-acetyl-cysteine, carnosine, gamma-glutamylcysteine, quercetin, lactoferrin, dihydrolipoic acid, citrate, Ginkgo Biloba extract, tea catechins, bilberry extract, vitamins E or esters of vitamin E, and retinyl palm itate.

The intraocular implants are intended to provide a therapeutically effective amount of the prostamide directly to an ocular region of the eye, preferably the anterior chamber, for 2-4 months or longer. Thus, with a single administration of the implant, a therapeutically effective amount of a prostamide will be made available at the site where it is needed and will be maintained for an extended period of time, rather than subjecting the patient to repeated injections or, in the case of self-administered eye drops, the burden of daily dosing.

The implant may be monolithic, i.e. having the active agent (for example bimatoprost) homogenously distributed throughout the polymeric matrix. Alternatively, the active agent may be distributed in a non-homogenous pattern in the polymer matrix. For example, an implant may include a portion that has a greater concentration of the prostamide compound relative to a second portion of the implant.

One example of an intraocular implant (i.e., drug delivery system) within the scope of the present invention is an extruded biodegradable intraocular implant sized for implantation in the anterior chamber of an eye, the implant comprising or consisting of 20% by weight (w/w) bimatoprost, 5% by weight PEG 3350, 20% by weight R203S, which is an ester-end poly(D,L-lactide) polymer having an inherent viscosity of 0.25-0.35 dl/g, 15% by weight R202H, which is an acid-end poly(D,L-lactide) polymer having an inherent viscosity of 0.16-0.24 dl/g, and 40% by weight RG752S, which is an ester-end poly(D,L-lactide-co-glycolide) polymer having a D,L-lactide:glycolide molar ratio of about 75:25 and an inherent viscosity of 0.16-0.24 dl/g, wherein the inherent viscosity of each polymer is measured for a 0.1% w/v solution in chloroform at 25° C. The implant may sustain release of a therapeutically effective amount of the bimatoprost into an eye for a period of two months or longer.

In some embodiments the intraocular implant is sized and formulated for placement in the anterior chamber of the eye (i.e., for intracameral administration). An implant sized for placement in the anterior chamber of an eye and capable of delivering a therapeutically effective amount of bimatoprost to the mammalian eye for an extended period according to this disclosure is generally from 20 µg to 200 µg in total weight, from 0.5 to about 3.0 mm in length, and from 0.1 to 0.5 mm in diameter (or other smallest dimension as may be appropriate for non-cylindrical implants). In some embodiments, an implant sized for placement in the anterior chamber (an intracameral implant) may weigh (therefore have a total weight) from about 30 to about 150 and contain from about 6 µg to about 30 µg of bimatoprost or other prostamide. In a preferred embodiment, the intracameral implant has a total weight of from 30 to 150 µg and is 150 µm to 300 µm in diameter and 0.5 mm to 2.5 mm in length. In a more preferred embodiment the biodegradable intracameral implant according to this disclosure has a total weight of 30 µg to 100 µg and is 150 µm to 300 µm in diameter and 0.5 mm to 2.5 mm in length. In some embodiments, the implant is about 150 to about 300 µm in diameter or width, about 1.0 mm to about 2.5 mm in length, and about 30 µg to about 100 µg in total weight. In some embodiments, the implant is 150 to about 300 µm in diameter or width, 1.0 mm to 2.5 mm in length, and 30 µg to 75 µg, or 30 to 90 µg in total weight. The implant may be an extruded implant (i.e., the implant may be produced by an extrusion process). In some embodiments, the implant is formed by an extrusion process and is 150 to 300 µm in diameter or width, 0.50 to 2.5 mm in length, and 30 to 100 µg in total weight.

Thus, an intracameral implant according to this disclosure may have a total weight of from 20-120 µg, 30-100 µg, 30-90 µg, 30-75 µg, or 30-50 µg. Non-limiting examples include extruded implants containing about 6 µg, 10 µg, 15 µg, or 20 µg (±5%) bimatoprost and having a total weight of about 30 µg, 50 µg, 75 µg, or 100 µg (±5%), respectively. In certain forms the extruded implant may have a diameter of about 200 µm or 250 µm (±5%) (before placement in the eye or other liquid or fluid environment) and a length of about 2.3 mm, 1.5 mm, or 1.0 mm (±5%). Preferably, the implant can be received in, and injected into the eye through, a 27, 28, or 30 gauge ultra-thin-wall needle. Small diameter needles such as these may be desirable for delivery of implants into the anterior chamber of the eye. Implants of the particular size described here may have the additional advantage of fitting within the anterior chamber angle of the eye without causing corneal trauma (e.g. edema) and without chaffing the iris. In one embodiment the intracameral implant is about 200 µm to about 300 µm in diameter, and about 1.0 to about 2.3 mm in length. An implant sized for placement in the anterior chamber of an eye according to this disclosure and according to any of the foregoing embodiments can comprise 20% (w/w) bimatoprost, 20% (w/w) R203S, 15% (w/w) R202H, 40% (w/w) RG752S, and 5% (w/w) polyethylene glycol (PEG) 3350. Implants are sized and formulated for placement in the anterior chamber in accordance with this disclosure so as to avoid contact with the corneal endothelium (i.e., so that the implant does not contact the corneal endothelium) after placement in the anterior chamber of an eye. Contact with the corneal endothelium may result in a loss of corneal endothelial cells (density reduction) and onset of corneal edema. The risk for such adverse effects generally rises with increasing size of the implant. With larger implants there is a greater likelihood of contact with the corneal endothelium, e.g., by touching the endothelium anterior to Schwalbe's line.

One embodiment is an extruded biodegradable intraocular implant according to this disclosure that is sized for placement in the anterior chamber of the eye, whereby the implant is 150 to 300 µm in diameter, 0.50 to 3 mm in length, and 25 to 100 µg in total weight. Another embodiment is an extruded biodegradable intraocular implant according to this disclosure that is sized for placement in the anterior chamber of the eye, whereby the implant is 150 to 250 μm (±5%) in diameter, 0.75 to 2 mm in length, and 50 to 75 μg in total weight. The implant according to either embodiment will usually comprise 20% by weight bimatoprost as the active agent in association with a biodegradable polymer matrix comprising or consisting of i) an ester-end poly(D,L-lactide), ii) an acid-end poly(D,L-lactide), and iii) an ester-end poly(D,L-lactide-co-glycolide) having a D,L-lactide:glycolide ratio of about 75:25 and an inherent viscosity of 0.16-0.24 dl/g, wherein the inherent viscosity is measured for a 0.1% solution of the polymer in chloroform at 25° C. In a more specific embodiment, the ester end poly(D,L-lactide) has an inherent viscosity of 0.25-0.35 dl/g and the acid-end poly(D,L-lactide) has an inherent viscosity of 0.16-0.24 dl/g.

The vitreous body of the eye may be able to accommodate relatively larger implants with total weights ranging from 250-5000 μg, and with diameters ranging from 0.5 mm to 3 mm and lengths ranging from 5 to 10 mm. If desired, an implant sized for placement in the anterior chamber may also be used for placement in the vitreous body of an eye.

The size and geometry of the implant can also be used to control the rate of release, period of treatment, and drug concentration at the site of implantation. Larger implants will deliver a proportionately larger dose, but depending on the surface to mass ratio, may have a slower release rate. The particular size and shape of the implant are chosen to suit the site of implantation, and may also be consistent with the size of the needle used to inject the implant into the eye.

The implants of this invention may be produced in a variety of shapes, including as a rod, sheet, film, wafer, or compressed tablet, but are preferably in the form of an extruded rod. An extruded rod may be cylindrical or non-cylindrical in shape. The implants may be monolithic, i.e. having the active agent or agents homogenously distributed through the polymeric matrix.

An implant according to this disclosure may desirably provide a substantially constant rate of prostamide release from the implant over the life of the implant. For example, it may be desirable for the prostamide to be released in an amount between 0.01 μg and 2 μg per day until 80-100% of the drug load has been released. However, the release rate may change to either increase or decrease depending on the formulation of the biodegradable polymer matrix. In addition, the release profile of the prostamide component may include one or more linear portions.

A therapeutically effective amount of bimatoprost for reducing intraocular pressure in an eye of a patient may correspond to a bimatoprost release rate in the eye of about 50 to 500 ng/day. An implant according to Formulation 2, for example (Table 1), with a total weight of about 25 μg and comprising about 20% by weight bimatoprost (i.e., about 5 μg of bimatoprost) may release approximately 50 ng of bimatoprost per day following placement in the eye. A Formulation 2 implant having a total weight of about 250 μg and comprising about 50 μg of bimatoprost may release approximately 500 ng of bimatoprost per day following placement in the eye.

Release of the prostamide from a biodegradable polymer matrix may be a function of several processes, including diffusion out of the polymer, degradation of the polymer and/or erosion or degradation of the polymer. Some factors which influence the release kinetics of active agent from the implant can include the size and shape of the implant, the size of the active agent particles, the solubility of the active agent, the ratio of active agent to polymer(s), the method of manufacture, the surface area exposed, and the erosion rate of the polymer(s). For example, polymers may be degraded by hydrolysis (among other mechanisms), and therefore, any change in the composition of the implant that enhances water uptake by the implant will likely increase the rate of hydrolysis, thereby increasing the rate of polymer degradation and erosion, and thus, increasing the rate of active agent release. Equally important to controlling the biodegradation of the polymer and hence the extended release profile of the implant is the relative average molecular weight of the polymeric composition employed in the implant. Different molecular weights of the same or different polymers may be included in an implant to modulate the release profile.

The release kinetics of the implants described herein can be dependent in part on the surface area of the implants. A larger surface area may expose more polymer and active agent to ocular fluid, and may cause faster erosion of the polymer matrix and dissolution of the active agent particles in the fluid. Therefore, the size and shape of the implant may also be used to control the rate of release, period of treatment, and active agent concentration at the site of implantation. As discussed herein, the matrix of the intraocular implant may degrade at a rate effective to sustain release of an amount of bimatoprost or other prostamide for two months after implantation into an eye.

The release rate of an active agent, such as bimatoprost, from an implant may be empirically determined using a variety methods. A USP approved method for dissolution or release test can be used to measure the rate of release (USP 23; NF 18 (1995) pp. 1790-1798). For example, using the infinite sink method, a weighed sample of the drug delivery system (e.g., implant) is added to a measured volume of a solution containing 0.9% NaCl in water (or other appropriate release medium such as phosphate buffered saline), where the solution volume will be such that the drug concentration after release is less than 20%, and preferably less than 5%, of saturation. The mixture is maintained at 37° C. and stirred slowly to ensure drug release. The amount of drug released in to the medium as a function of time may be quantified by various methods known in the art, such as spectrophotometrically, by HPLC, mass spectroscopy, etc.

The intraocular implants described here comprise a mixture of at least three different biodegradable polymers selected from the group consisting of poly(D,L-lactide) (PLA) polymers and poly(D,L-lactide-co-glycolide) (PLGA) polymers. Differences between the three polymers may be with regard to the end group, inherent viscosity, or repeating unit, or any combination thereof.

Poly (D,L-lactide), or PLA, may be identified by CAS Number 26680-10-4, and may be represented by the formula:

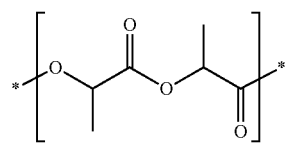

Poly(D,L-lactide-co-glycolide), or PLGA, may be identified by CAS Number 26780-50-7, and may be represented by the formula:

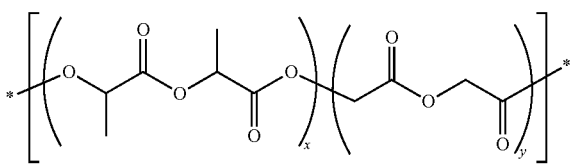

Thus, poly(D,L-lactide-co-glycolide) comprises one or more blocks of D,L-lactide repeat units (x) and one or more blocks of glycolide repeat units (y), where the size and number of the respective blocks may vary. The molar percent of each repeat unit in a poly(lactide-co-glycolide) (PLGA) copolymer may be independently 0-100%, 50-50%, about 15-85%, about 25-75%, or about 35-65%. In some embodiments, the D,L-lactide may be about 50% to about 85% of the PLGA polymer on a molar basis. The balance of the polymer may essentially be the glycolide repeat units. For example, the glycolide may be about 15% to about 50% of the PLGA polymer on a molar basis.

More specifically the at least three different biodegradable polymers included in an intraocular implant according to this disclosure are independently selected from the group consisting of:
 a) a poly(D,L-lactide) having an acid end group and an inherent viscosity of 0.16-0.24 dl/g, as measured for a 0.1% solution in chloroform at 25° C. (such as for example R202H);
 b) a poly(D,L-lactide) having an ester end group and an inherent viscosity of 0.25-0.35 dl/g, as measured for a 0.1% solution in chloroform at 25° C. (such as for example R203S);
 c) a poly(D,L-lactide-co-glycolide) having an acid end group, an inherent viscosity of 0.16-0.24 dl/g (as measured for a 0.1% solution in chloroform at 25° C.), and a D,L-lactide:glycolide molar ratio of about 50:50 (such as for example RG502H);
 d) a poly(D,L-lactide-co-glycolide) having an ester end group, an inherent viscosity of 0.16-0.24 dl/g (as measured for a 0.1% solution in chloroform at 25° C.), and a D,L-lactide:glycolide molar ratio of about 50:50 (such as for example RG502);
 e) a poly(D,L-lactide-co-glycolide) having an ester end group, an inherent viscosity of 0.16-0.24 dl/g (as measured for a 0.1% solution in chloroform at 25° C.), and a D,L-lactide:glycolide molar ratio of about 75:25 (such as for example RG752S);
 f) a poly(D,L-lactide-co-glycolide) having an ester end group, an inherent viscosity of 0.50-0.70 dl/g (as measured for a 0.1% solution in chloroform at 25° C.), and a D,L-lactide:glycolide molar ratio of about 75:25 (such as for example RG755S); and
 g) a poly(D,L-lactide-co-glycolide) having an ester end group, an inherent viscosity of 1.3-1.7 dl/g (as measured for a 0.1% solution in chloroform at 25° C.), and a D,L-lactide:glycolide molar ratio of about 85:15 (such as for example RG858S).

Unless otherwise specified, the inherent viscosities of the PLA and PLGA polymers referred to in this disclosure are determined for a 0.1% (w/v) solution of the polymer in chloroform ($CHCl_3$) at 25° C. Biodegradable PLA and PLGA polymers, such as the RESOMER® Biodegradable Polymers R203S, R202H, RG752S, RG755S, and RG858S, are available commercially from sources such as Evonik Industries, AG, Germany (Evonik Rohm Pharma GmbH), and Sigma-Aldrich.

Bimatoprost is described in, for example, U.S. Pat. Nos. 6,403,649 and 5, 688,819, both of which are herein incorporated by reference.

In addition to bimatoprost and the at least three different biodegradable polymers, some implants according to this disclosure further include a polyethylene glycol having a molecular weight of 300 Da to 20,000 Da. For example, an implant may comprise polyethylene glycol 3350 (PEG 3350), or alternatively polyethylene glycol 20,000 (PEG 20K).

The prostamide component of the implant may be in a particulate or powder form and it may be entrapped by, embedded within, or distributed uniformly or non-uniformly throughout the biodegradable polymer matrix. In the presently disclosed implants, the prostamide will usually comprise about 20% of the implant on a weight to weight (w/w) basis. In other words, the prostamide will constitute about 20% of the implant by weight. More generally, the prostamide can comprise (i.e., be present in an amount of or constitute) 18% and 22% of the implant by weight.

In addition to bimatoprost or other prostamide, the intraocular implants and other drug delivery systems (e.g., microspheres) disclosed herein may optionally include one or more buffering agents, preservatives, antioxidants, or other excipients, or combinations thereof. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between 2 to 9 and more preferably 4 to 8. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These buffering agents, preservatives, antioxidants, and other excipients may be present in amounts of from 0.001 to 10% by weight of the implant.

Examples of antioxidant agents include ascorbate, ascorbic acid, alpha-tocopherol, mannitol, reduced glutathione, various carotenoids, cysteine, uric acid, taurine, tyrosine, superoxide dismutase, lutein, zeaxanthin, cryptoxanthin, astaxanthin, lycopene, N-acetyl-cysteine, carnosine, gamma-glutamylcysteine, quercitin, lactoferrin, dihydrolipoic acid, citrate, Ginkgo Biloba extract, tea catechins, bilberry extract, vitamins E or esters of vitamin E, and retinyl palmitate.

An implant according to this invention may comprise a single type of prostamide compound (for example, bimatoprost) as the sole active agent or may comprise a combination of two or more prostamides.

The biodegradable implants of the present invention may be sterilized by gamma or by electron-beam radiation and inserted or placed into the anterior chamber or vitreous body of an eye by a variety of methods and devices, including needle-equipped delivery devices capable of ejecting the implant into the ocular region of the eye. An effective dose of radiation for sterilization may be about 20-30 kGy. One example of a device that may be used to insert an implant into an eye is disclosed in U.S. Pat. No. 6,899,717. The ocular applicator or injection device will generally comprise an appropriately sized needle. Smaller needles are preferred to minimize trauma to the eye (for example, a 25, 27, 28, or 30 gauge needle). In some embodiments, the hand held applicator comprises an 25-30 gauge stainless steel needle, a lever, an actuator, and a plunger or push rod to promote ejection of the implant from the device into the eye. Some embodiments comprise placing two implants in an ocular region of the eye, such as for example the anterior chamber or vitreous body of the eye.

Figure 7:
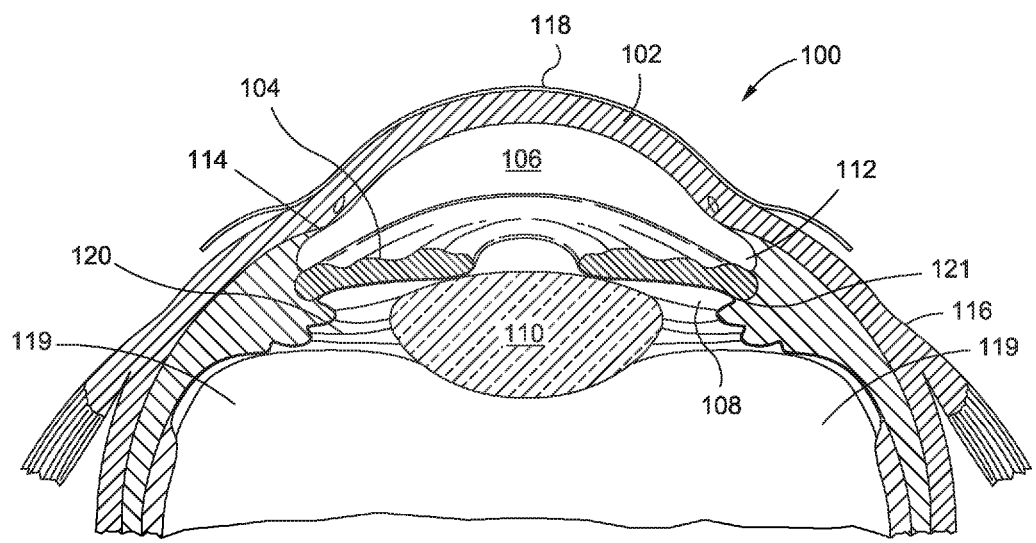
FIG. 7 shows a cross-section of the mammalian eye.

To provide for the intended therapeutic effect (e.g., long term reduction of intraocular pressure) in a patient, including one suffering from glaucoma, an implant according to the present invention can be placed in the anterior chamber of the eye. The anterior chamber refers to the space inside the eye between the iris and the innermost corneal surface (endothelium). In some patients, however, such as those with a narrow anterior chamber angle, it may be preferable to place the implant in the vitreous body of the eye. Other possible locations for an implant include the subconjunctival space, subtenon's space, and the posterior chamber, which is the space inside the eye between the back of the iris and the front face of the vitreous. The posterior chamber includes the space between the lens and the ciliary processes, which produces the aqueous humor that nourishes the cornea, iris, and lens and maintains intraocular pressure. Referring to FIG. 7, these and other ocular regions of the eye (100) are shown in cross-section. Particular regions of the eye (100) include the cornea (102) and iris (104), which surround the anterior chamber (106). Behind the iris (104) is the posterior chamber (108) and lens (110). Within the anterior chamber is the anterior chamber angle (112) and trabecular meshwork (114). Also shown are the corneal epithelium (118), sclera (116), vitreous (119), ciliary zonules (120), and ciliary process (121). The posterior segment of the eye is the rear two-thirds of the eyeball (behind the lens), and includes the vitreous, the retina, and the optic nerve.

The method of implantation may involve accessing the target area within the ocular region with the needle, or implantation device. Once within the target area, e.g., the anterior chamber or vitreous cavity, a lever on a hand held device can be depressed to cause an actuator to drive a plunger or push rod or other suitable means forward. As the plunger moves forward, it can push the implant or implant into the target area. The location of the implant may influence the concentration gradients of drug surrounding the implant, and thus influence the release rates (e.g., an implant placed in the vitreous, a viscous gel, may result in a slower release rate compared with placement in the aqueous humor (i.e. non-viscous water)). In some forms of the method for treating a patient according to this disclosure it may be desirable to place the implant in the anterior vitreous. For vitreous placement, the anterior vitreous may be ideal since it remains viscous throughout a patient's life time. As a result, this viscous environment entraps the implant and maintains the implant adjacent to the target tissues (i.e. ciliary body) to maximize the prostamide pharmacologic activity. In contrast, the posterior vitreous can liquefy with age and does not necessarily provide reasonable implant proximity to the ciliary body to optimize the pharmacologic performance of the implant.

Various techniques may be employed to make biodegradable intraocular implants. Useful techniques include extrusion methods (for example, hot melt extrusion), compression methods, pellet pressing, solvent casting, print technology, hot embossing, soft lithography molding methods, injection molding methods, heat press methods and the like. As previously discussed, a biodegradable intraocular implant according to this disclosure may be configured as a rod, wafer, sheet, film, or compressed tablet. Cast films or sheets can be ground into microparticles, which may be useful in some applications. Biodegradable microspheres formed by an emulsion method and having any of the formulations described herein may also find use in a method according to this disclosure.

Preferably the intraocular implant of this disclosure is a solid rod-shaped implant formed by an extrusion process (an extruded rod) and is sized for placement in the anterior chamber of the eye. Methods for making a bimatoprost-containing intraocular implant by an extrusion process are familiar to those of skill in the art. See, for example, US 2008/0145403 and US 2005/0244464. An extruded implant (e.g., an extruded rod) can be made by a single or double extrusion method. Choice of technique, and manipulation of technique parameters employed to produce the implants can influence the release rates of the drug. Room temperature compression methods may result in an implant with discrete microparticles of drug and polymer interspersed. Extrusion methods may result in implants with a progressively more homogenous dispersion of the drug within a continuous polymer matrix, as the production temperature is increased. The use of extrusion methods may allow for large-scale manufacture of implants and result in implants with a homogeneous dispersion of the drug within the polymer matrix.

The temperature used during an extrusion method should be high enough to soften the polymer but low enough to avoid substantial loss of prostamide activity. In this regard, extrusion methods may use temperatures of 50° C. to 130° C., but more preferably the extrusion temperature is between 50° C. and 80° C., or even more preferably from 55° C. to 70° C., particularly for the production of implants comprising bimatoprost. For example, the extrusion temperature used to make a bimatoprost-containing implant or other prostamide-containing implant may be 60° C. to 75° C., or from 60° C. to 70° C. Low temperatures such as these may be preferred for a variety of prostamides, including bimatoprost, to best preserve their potency through to the final extruded implant.

Different extrusion methods may yield implants with different characteristics, including but not limited to the homogeneity of the dispersion of the active agent within the polymer matrix. For example, using a piston extruder, a single screw extruder, and a twin screw extruder may produce implants with progressively more homogeneous dispersion of the active agent. When using one extrusion method, extrusion parameters such as temperature, feeding rate, circulation time, pull rate (if any), extrusion speed, die geometry, and die surface finish will have an effect on the release profile of the implants produced.

In one variation of producing implants by a piston or twin-screw extrusion methods, the drug and polymers, including any polyethylene glycol if called for, are first mixed at room temperature and then heated to an appropriate temperature to soften the mixture or transform the mixture to a semi-molten state for a time period of 0 to 1 hour, for 1 to 10 minutes, 1 minute to 30 minutes, 1-5 minutes, 5 minutes to 15 minutes, or 10 minutes. The implants are then extruded at a temperature of between 50° C. and 80° C. In some variations, the temperature of extrusion may range from 60-75° C., or from 60-65° C. In some screw extrusion methods, the powder blend of active agent and polymer is added to a single or twin screw extruder preset at a temperature of 50° C. to 130° C., and directly extruded as a filament or rod with minimal residence time in the extruder. The extruded filament is then cut to a length suitable for placement in the anterior chamber or vitreous of the eye. The total weight of the implant will of course be proportional to the length and diameter of the implant, and implants may be cut to a desired target weight and therefore dosage of the bimatoprost. For example, an intracameral implant in accordance with this disclosure may be cut to a target weight of between 20 and 150 μg (±5%). In some embodiments, the implants are cut to a target weight of 50 μg (±5%), 75 μg (±5%), or 100 μg (±5%), wherein 20% of the implant by weight is bimatoprost.

Compression methods may use pressures of 50-150 psi, more preferably 70-80 psi, even more preferably about 76 psi, and use temperatures of 0° C. to 115° C., more preferably about 25° C.

In one embodiment, the method for making the implants involves dissolving the appropriate polymers and therapeutic prostamide in a solvent. Solvent selection will depend on the polymers and therapeutic agents chosen. For the implants described herein, including a therapeutic agent such as bimatoprost, dichloromethane (DCM) is an appropriate solvent. Other solvents may include methylene chloride and ethyl acetate. Once the polymers and therapeutic agent(s) have been dissolved, the resulting mixture is cast into a die of an appropriate shape. Once cast, the solvent used to dissolve the polymers and therapeutic agent(s) is evaporated at a temperature between 20° C. and 30° C., preferably about 25° C. The polymer can be dried at room temperature or even in a vacuum. For example, the cast polymers including therapeutic agents can be dried by evaporation in a vacuum. Once the cast polymers are dried, they can be processed into an implant using any method known in the art to do so. In an example embodiment, the dried casted polymer can be cut and/or ground into small pieces or particles and extruded into rounded or squared rod shaped structures at a temperature between 50° C. and 80° C.

Compared with existing implants, an implant of this invention is preferably substantially completely degraded in less than 5 months, less than 10 months, or less than 12 months after placement in an eye. An implant is substantially completely degraded when no more than 5% of the original mass of the implant remains in the eye or when the molecular weight of the degraded polymers falls below 1000 Daltons. The rate of degradation and consequently the predicted lifetime of an implant in vitro may, for example, be measured for the implant in 0.01M PBS (pH 7.4) under constant shaking at 37° C.

Compared with existing implants, an implant of this invention, when placed in an eye, preferably swells to a diameter no greater than four times its original diameter and/or to a length no greater than two times its original length.

An intraocular implant of this disclosure, whether placed in the anterior chamber or vitreous of the eye, may be effective in reducing intraocular pressure in the eye for 2-6 months or for 2-9 months, or even for 2-12 months or longer after placement in the eye without causing corneal edema. One embodiment includes a method for delaying, slowing, or inhibiting visual field loss or for improving vision in an eye of a patient with glaucoma comprising placing a biodegradable intraocular implant according to this disclosure in the anterior chamber or vitreous body of the eye, thereby reducing intraocular pressure in the eye continuously for 4-12 months or 6-12 months.

The present disclosure provides for a biodegradable intraocular implant for reducing intraocular pressure (IOP) in an eye comprising a biodegradable polymer matrix, polyethylene glycol 3350, and a prostamide as the active agent, wherein the prostamide and polyethylene glycol 3350 are associated with the biodegradable polymer matrix, which comprises an ester end poly(D,L-lactide) having an inherent viscosity of 0.25-0.35 dl/g, an acid end poly(D,L-lactide) having an inherent viscosity of 0.16-0.24 dl/g, and an ester end poly(D,L-lactide-co-glycolide) having an inherent viscosity of 0.16-0.24 dl/g and a D,L-lactide to glycolide molar ratio of about 75:25, wherein the prostamide constitutes 18 to 22% of the implant by weight, the ester end poly(D,L-lactide) constitutes 18 to 22% of the implant by weight, the acid end poly(D,L-lactide) constitutes 13.5 to 16.5% of the implant by weight, the ester end poly(D,L-lactide-co-glycolide) constitutes 36 to 44% of the implant by weight, and wherein the polyethylene glycol 3350 constitutes 3.5 to 6.5% of the implant by weight, wherein the inherent viscosity of each of the poly(D,L-lactide) and poly(D,L-lactide-co-glycolide) polymers is determined for a 0.1% solution of the polymer in chloroform at 25° C. In a specific embodiment the prostamide constitutes 20% of the implant by weight, the ester end poly(D,L-lactide) constitutes 20% of the implant by weight, the acid end poly(D,L-lactide) constitutes 15% of the implant by weight, the ester end poly(D,L-lactide-co-glycolide) constitutes 40% of the implant by weight, and the polyethylene glycol 3350 constitutes 5% of the implant by weight.

In some embodiments the implant defined above is rod-shaped and is formed by a hot-melt extrusion process such that the formed implant is 150 to 300 μm in diameter or width, 0.50 to 2.5 mm in length, and 30 to 100 μg in total weight, whereby the implant does not contact the corneal endothelium after placement in the anterior chamber of an eye. The implant is preferably effective for reducing intraocular pressure in an eye for 2 months or longer after placement in the eye. In one form of the implant, the prostamide is bimatoprost.

Example

Manufacture and Testing of Intracameral Implants Comprising Bimatoprost and a Biodegradable Polymer Matrix We set out to identify a solid biodegradable intracameral implant that would not only release a therapeutically effective level of bimatoprost for an extended period (preferably two months or longer) but one that would also fit into the anterior chamber angle of the eye without injuring the corneal endothelium or chaffing the iris. We realized that it was important to avoid injuring the corneal endothelium as this can lead to inflammation and possibly corneal opacity and corneal edema, due possibly to mechanical trauma to the corneal endothelium by the implant. Accordingly, the size of the implant and therefore the diameter (or width) and length of the implant were carefully considered during the development of the implant.

Other properties considered included 1) the rate and duration of drug release from the implant; a linear drug release profile is preferred; 2) the extent to which the implant swells when placed in aqueous media (as compared to the initial size of the implant); polymer formulations that take on or absorb less fluid are more likely to fit into the anterior chamber angle and remain compatible with this space during the lifetime of the implant; and 3) the time it takes for the implant to completely degrade after drug release is completed (i.e., the biodegradation time of the implant). Ideally, the implant does not linger in the eye long after its drug supply is depleted, but is degraded and eliminated from the eye soon after its drug supply has been exhausted.

Bimatoprost intracameral implants in this study were made by hot melt extrusion in a Haake or DSM twin-screw microcompounder/extruder. Other possible methods may include direct compression, single-screw extrusion, solvent casting, injection molding, soft lithography, hot embossing, and print technology. The extruded implants in this study were rod-shaped, but they can be made into any geometric shape by changing the extrusion or compression die. Biodegradable polymers (such as the RESOMER® polymers, designated by polymer number in the Tables below) were used as received from polymer suppliers, such as Evonik Industries.

The implants were made by combining bimatoprost with the biodegradable polymers in a stainless steel container with two 10-mm stainless steel balls and mixed for 15 minutes in a Turbula mixer. The container was removed from the mixer and the powder blend was stirred with a spatula. The powder blend was inspected for homogeneity and the mixing procedure was repeated. The twin-screw microcompounder/extruder was set up according to the manufacturer's instructions. The output of the extruder was fitted with a laser micrometer and a puller to control the thickness of the extruded filament. The twin-screw microcompounder/extruder was allowed to equilibrate to the extrusion temperature; then the powder blend was fed into the extrusion screws at a rate that maintained a constant load and torque. A filament was extruded into a guide mechanism and cut into individual implants (rods) with a specific length so as to obtain a desired target weight (±5%) and drug dosage for the implant. For example, implants containing 10 µg, 15 µg, and 20 µg bimatoprost can be made by cutting the extruded filaments to a target weight of 50±2.5 µg (5%), 75±3.75 µg (5%), and 100±5 µg (5%), respectively.

Tables 1 and 2 summarize the drug and polymer composition (Formulation) of some of the implants made and tested during this study. Formulation 1 has been previously described in US Patent Application Publication 2011/0182966, which is herein incorporated by reference. Table 3 summarizes results for some of the implants. For each implant we measured 1) the rate of bimatoprost release from the implant in vitro over time into a release medium consisting of 0.01M phosphate buffered saline (PBS), pH 7.4, at 37° C. (calculated and plotted for replicate implants as the percent average total bimatoprost release over time), 2) the degree and extent of implant swelling over time in 0.01M phosphate buffered saline (PBS), pH 7.4 at 37° C., and 3) the rate of implant degradation in 0.01M phosphate buffered saline (PBS), pH 7.4 at 37° C. The estimated in vitro lifetime of an implant was determined for each implant formulation based on the degradation results. For in vivo testing the implants were placed in a vial and sterilized by a gamma radiation dose of 25 to 40 kGy.

Previous studies had taught us that implants containing more than 30% by weight bimatoprost often produce a "burst" of bimatoprost release upon immersion in a specific release medium such as PBS. On the other hand, for implants containing less than 20% by weight bimatoprost, the release of bimatoprost is sometimes delayed resulting in an undesirable lag period between the time the implant is placed in release medium and the time significant quantities of bimatoprost begin appearing in the medium. Accordingly, for purposes of formulating the intracameral sustained release implant and obtaining the desired target drug release profile, all implants prepared for this study contained 20% by weight bimatoprost.

As shown by the results below, we identified a polymer formulation (Formulation No. 2) that can provide for the sustained release of bimatoprost in vitro at a near linear rate (approximately half-order release kinetics) for approximately 60 days without an initial burst effect or lag period (FIG. 1). The release rate is slightly faster than the implant having Formulation No. 1. Moreover, the implant having Formulation No. 2 represents a significant improvement over Formulation No. 1 for reasons discussed below, particularly for intracameral implants that tend to settle inferiorly into the anterior chamber angle of the eye.

Figure 2A:
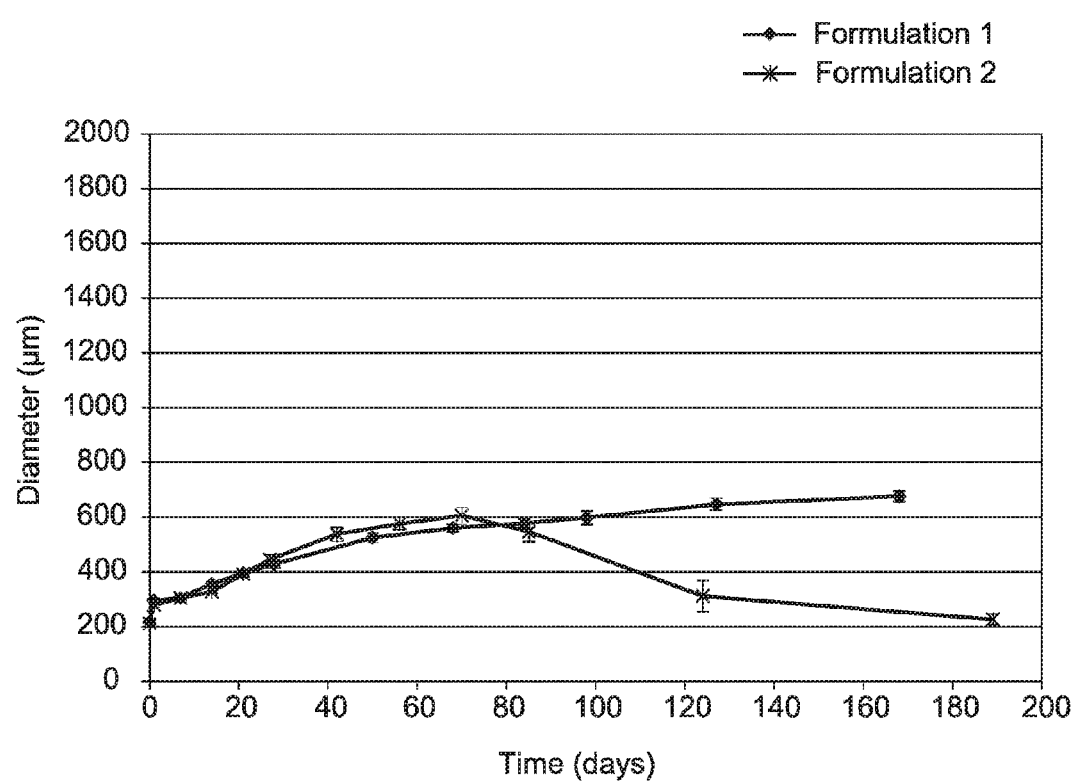
FIGS. 2A and B show the change in diameter and length (i.e., the swelling) of an extruded implant having either Formulation 1 or Formulation 2 over time in 0.01 M phosphate buffered saline (pH 7.4) at 37° C. The starting weight of the implants was about 50 μg, and the initial length and diameter of the implants in these studies were about 1.05 mm and about 200 μm, respectively.
Figure 3:
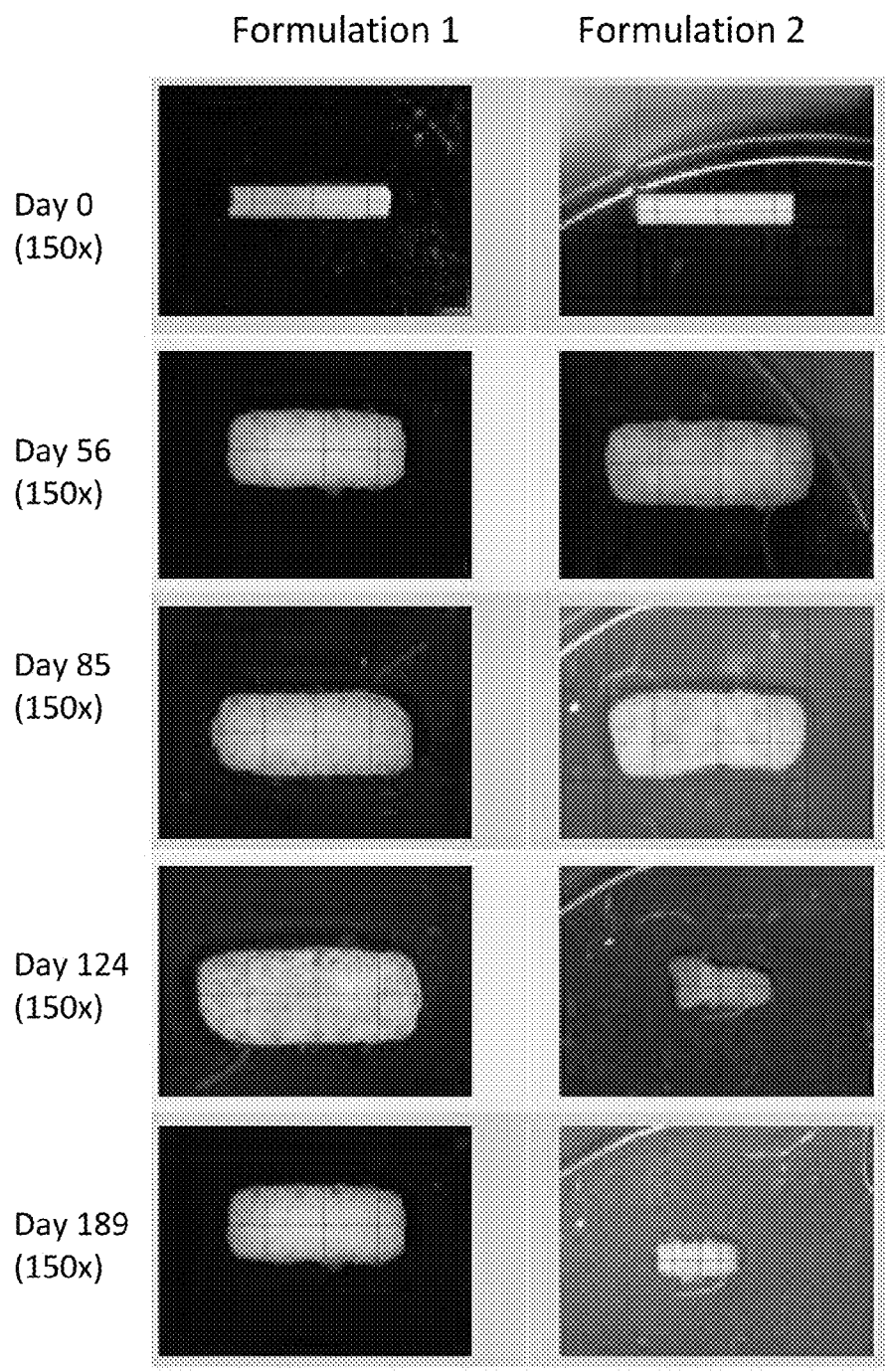
FIG. 3 shows the swelling and degradation of extruded implants having either Formulation 1 or Formulation 2 in vitro over time following placement of the implants in phosphate buffered saline (pH 7.4) at 37° C. The implant mages were recorded at a magnification of 150× at various time points and the lengths and diameters were measured. Each implant was initially 1.05 mm in length and 200 μm in diameter and the starting total weight of each implant was about 50 μg.

Surprisingly, we found that by adjusting the proportions of the three biodegradable polymers (R203S, RG752S, and R202H) present in our original three polymer drug delivery system (Formulation 1), we could dramatically reduce the in vitro lifetime of the implant (Table 3) while maintaining the near linear rate of drug release over the approximate 60 day period we had earlier observed for Formulation 1 (FIG. 1). As shown in Table 3, an implant having Formulation 2 degrades nearly twice as fast in vitro as an implant having Formulation 1. Moreover, the moderate adjustment in polymer composition from Formulation 1 to Formulation 2 also improved the swelling behavior of the implant (FIGS. 2A and B). As shown in FIGS. 2A and B, the implant having Formulation 2 reaches a maximum swell diameter of about 550 to 600 µm and maximum length of about 1.5 mm approximately two months after placement in PBS (pH 7.4, 37° C.) and starts to contract thereafter, whereas the implant having Formulation 1 continues to swell even after two months, growing larger in both length and diameter over the next 3 to 4 months that the measurements were taken. The differences in degradation rate and swelling behavior for Formulation 1 and 2 implants are also visually evident in the microscope images of these implants shown in FIG. 3. We considered the low swell, rapid degradation characteristics of Formulation 2 to be ideal for an intracameral implant that would ultimately settle or be specifically placed in the anterior chamber angle of the eye of a patient with glaucoma or ocular hypertension. Furthermore, the near linear, long term release of bimatoprost observed for this implant in vitro, suggested that an extruded implant having Formulation 2 would be effective for lowering intraocular pressure in an eye for an extended period, perhaps as long as two months or more, after placement in the anterior chamber of the eye.

In vitro drug release testing was performed by incubating the implants in 2 mL of 0.01M PBS pH 7.4 (1 implant per vial) in a shaking water bath set at 37° C. and 50 rpm. A sample was taken at 24 hours, and then every week for the first month, and then bi-weekly thereafter. The release medium was replaced with fresh medium during each sampling time point and the concentration of bimatoprost in the PBS was quantified using the HPLC. The bimatoprost release profiles for implants having Formulation 1 and 2 (Table 1) are shown in FIG. 1. Data points represent the average release of 3 to 4 replicate implant samples.

In vitro polymer degradation testing was performed by incubating implants in 0.01 M PBS pH 7.4 in a shaking water bath set at 37° C. For each formulation, 20 implants that were each approximately 6 mm length were incubated in triplicates for a duration of 8 weeks. Samples were taken weekly. The peak molecular weight (MW) was determined using a GPC equipped with an R.I. detector and polystyrene as a standard. Degradation rate constants were calculated from the $1^{st}$ order kinetic curves to determine the in-vitro polymer degradation rate constants for all formulations. The rank order of the formulations based on the total kinetic rate constants and the estimated in-vitro life times ($t_{1000}$) for each implant formulation are summarized in Table 3. $T_{1000}$ represents the time at which the molecular weights of the polymers in the implant are expected to fall below 1000 Daltons.

Figure 2B:
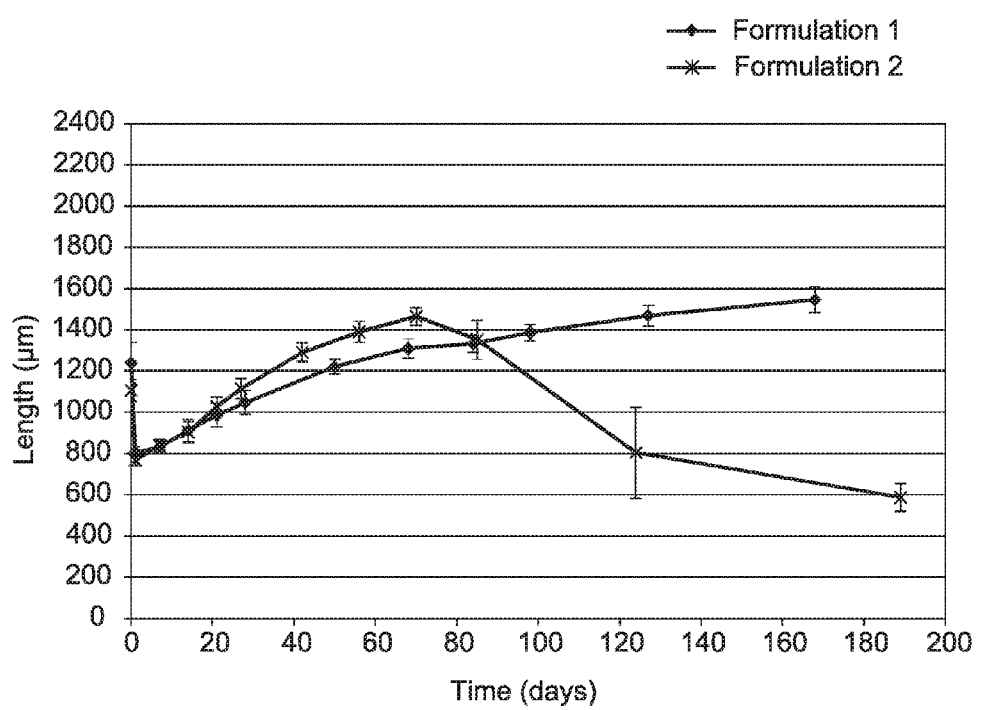

For the implant swelling study (FIGS. 2A, 2B, and 3 and Table 3), each implant was incubated in approximately 400 μL of PBS (pH 7.4, 0.01M) in Microwell 96-Well Assay Plates and placed in a Shake N Bake Hybridization Oven set at 37° C. and 50 rpm. Implant images were recorded at 150× magnification at each time point and the lengths and diameters were measured by Keyence Digital Microscope. Images were recorded at initialization, then weekly for the first month, and biweekly thereafter.

Figure 4:
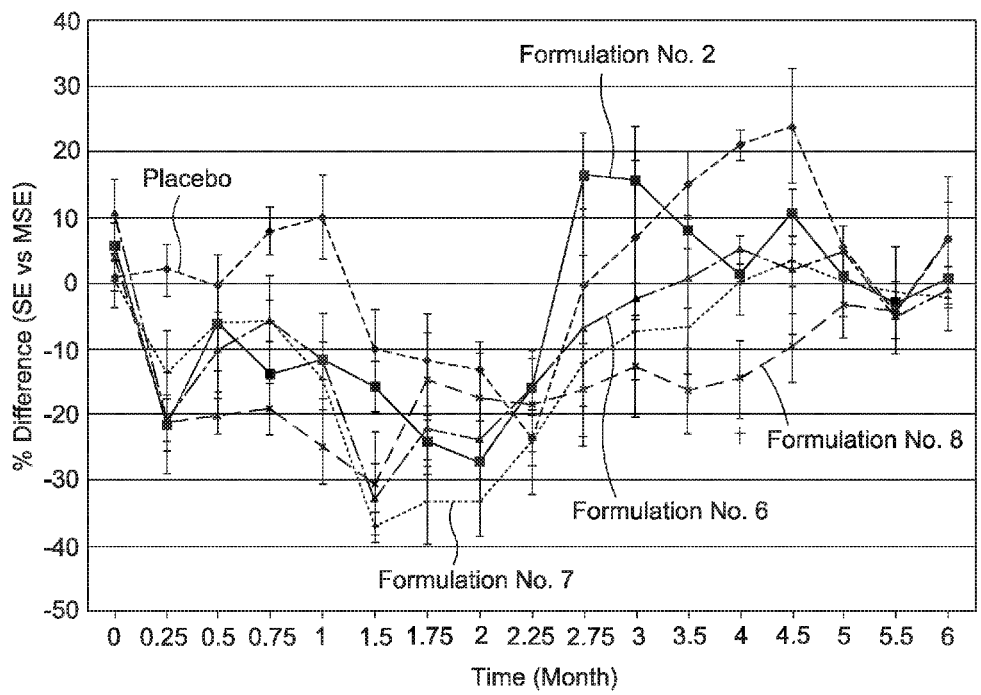
FIG. 4 shows the reduction in IOP in a dog eye following intracameral injection of a bimatoprost-containing implant.
Figure 5:
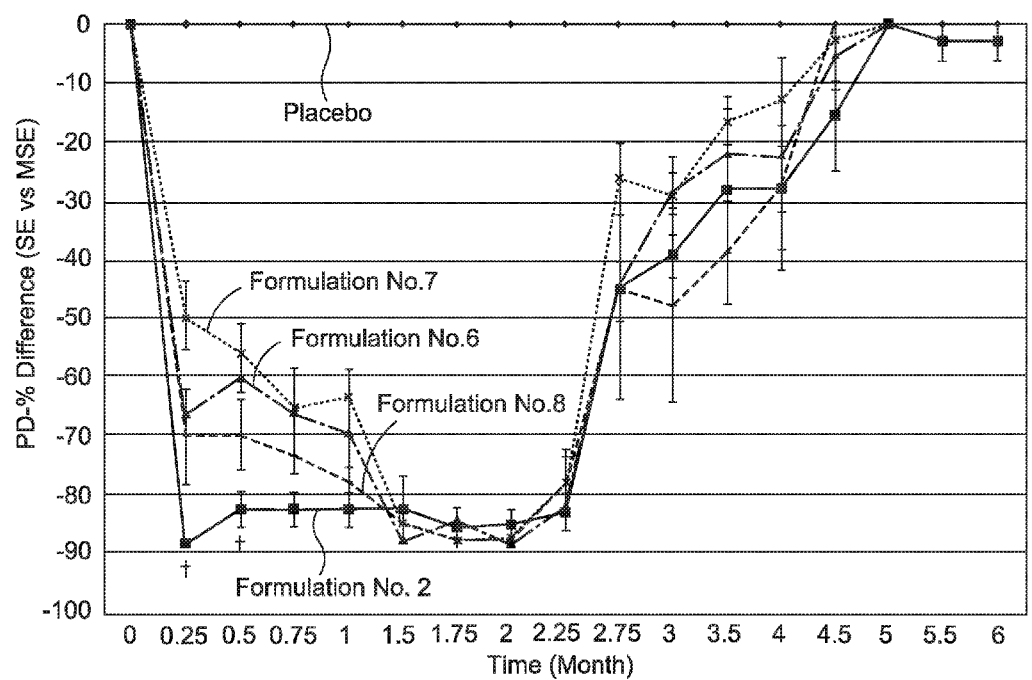
FIG. 5 shows the change in pupil diameter in a dog eye over time following the intracameral injection of a bimatoprost-containing implant.

An in vivo animal study in normal beagle dogs was conducted to evaluate the in vivo efficacy, tolerability, and safety of the implants. Four formulations (Table 4) were evaluated in dog groups 2, 3, 4, and 5. Group 1 received placebo implants. Each formulation was unilaterally dosed (OD) as a single 20-μg (dosage) implant; four dogs per formulation; fellow eyes as controls. IOP and Safety measurements were made weekly for 3 months, then bi-weekly up to 6 months. Efficacy was assessed by IOP and pupil diameter; tolerability by central corneal endothelial cell density, and corneal thickness, and anterior chamber flare and cells; and safety by ocular histology at 6 months. With regards to efficacy, all four formulations reduced IOP and pupil diameter (dogs become miotic with bimatoprost exposure) (FIGS. 4 and 5). Reduction in pupil diameter in dogs is an indication of bimatoprost exposure to the anterior chamber.

Insofar as the Implants described in Table 4, there were no differences between treated and fellow eyes for the following tolerability measures: central corneal endothelial cell density, central corneal thickness, nor anterior chamber flare and cells. The primary safety measure was histology and there were no changes in structure of the ocular tissues that were significant or adverse. These results with these implants (Table 4) show that single intracameral doses of the new formulations using this invention demonstrate excellent efficacy, tolerability, and safety.

A reduction in corneal endothelial cell density in the eye following injection of an implant into the anterior chamber indicates the implant is injuring the corneal endothelium. This occurs, for example, when the implant cannot fit within the anterior chamber angle because it is too large, causing it to rest and rub against the corneal endothelium, or because, even if it does fit within the angle, the implant swells to such an extent that it begins to contact and rub against the corneal endothelium. Irritation of the corneal endothelium in this way eventually leads to a loss of endothelial cell density at the focal center of the cornea, and possibly to focal opacity, corneal edema, and corneal neovascularization.

Figure 6:
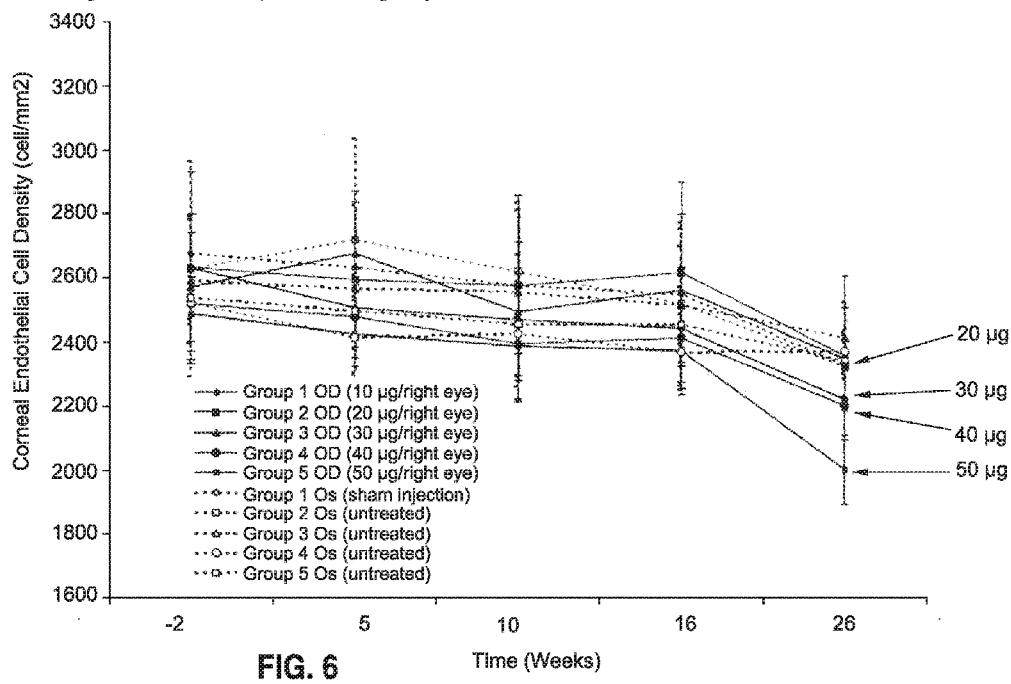
FIG. 6 shows the change in mean corneal endothelial cell density in an eye after receiving an extruded bimatoprost-containing implant in the anterior chamber. One implant was placed in the right eye of each dog in Groups 2, 3, 4, and 5. Each implant comprised Formulation 1 and contained 20, 30, 40, or 50 μg of bimatoprost, as shown in parentheses. The total weight of the injected implant was approximately 5 times (5×) the weight of bimatoprost, since each implant comprised about 20% bimatoprost by weight (see Formulation 1 in Table 1). Accordingly, animals in Groups 2, 3, 4, and 5 received implants that weighed about 100, 150, 200, and 250 μg, respectively. The x-axis shows time from dosing.

Focal corneal endothelial cell density was measured in dogs 2, 5, 10, 16, and 26 weeks after intracameral injection of a 100-μg, 150-μg, 200-μg, or 250-μg (total weight) implant prepared by an extrusion process and comprising Formulation 1. Treated animals (Groups 2-5) received one implant in the anterior chamber of the right eye while the left eye was left untreated. One group of dogs, Group 1, received no injection in either eye. As shown by FIG. 6, by week 26 a reduction in corneal endothelial cell density was observed in the animals receiving the 150-μg, 200-μg, and 250-μg implants. In contrast, there was no clinically significant reduction in the corneal endothelial cell density in dogs that received the 100-μg implant, which contained 20 μg of bimatoprost, as shown in FIG. 6. These results show that the size of the intracameral implant is an important consideration for the compatibility of the implant with the anterior chamber of the eye, and to ensure the implant will fit within the anterior chamber angle and cause no adverse effects such as edema or opacity long after placement in the eye.

TABLE 1

Bimatoprost Containing Sustained Delivery Formulations (1-5) for the production of extruded intracameral implants

| Formulation No. | Bimatoprost % w/w | Polymer, excipient % w/w | | | | |
|---|---|---|---|---|---|---|
| | | R203S | R202H | RG752S | RG858S | PEG 3350 |
| 1 | 20 | 45 | 10 | 20 | | 5 |
| 2 | 20 | 20 | 15 | 40 | | 5 |
| 5 | 20 | 15 | | 40 | 20 | 5 |

TABLE 2

Bimatoprost-containing Sustained Delivery Formulations (6-8) for the production of extruded intracameral implants

| Formulation No. | Bimatoprost % w/w | Polymer % w/w | | | | |
|---|---|---|---|---|---|---|
| | | RG752S | RG755S | RG502 | RG502H | RG858S |
| 3 | 20 | 35 | 15 | 15 | | 15 |
| 4 | 20 | 40 | | 5 | 5 | 30 |
| 6 | 20 | 20 | 50 | 5 | 5 | |
| 7 | 20 | 25 | 50 | 5 | | |
| 8 | 20 | 30 | | 20 | | 30 |

TABLE 3

In vitro Properties of select intracameral implants produced by an extrusion process

| Implant Formulation | Implant dimensions (diameter × length) and total weight | Duration of in vitro drug release | In vitro lifetime $t_{1000}$ (months) | Implant swelling in vitro (max) relative to initial size |
|---|---|---|---|---|
| 1 | 250 μm × 2.3 mm 150 μg | ~60 Days | 9-11 | Diameter: 2.7-3.0 X Length: 1.2X |
| 2 | 250 μm × 2.3 mm 150 μg | ~60 Days | 4-6 | Diameter: 2.7-3.0 X Length: 1.2X |
| 5 | 250 μm × 2.3 mm 150 μg | ~60 Days | 4-6 | Diameter: 2.7-3.0 X Length: 1.0X |
| 3 | 250 μm × 2.3 mm 150 μg | ~60 Days | 3-4 | Diameter: >4X Length: <0.5X |
| 4 | 250 μm × 2.3 mm 150 μg | ~60 Days | 3-4 | Diameter: >4X Length: <0.5X |

TABLE 4

Bimatoprost-containing extruded intracameral implants used for in vivo study in dogs

| Dog Group | Formulation No. | Bimatoprost Dose (μg) | Implant Morphology (shape) | Implant Dimensions (mm) | Total Implant Weight (μg) |
|---|---|---|---|---|---|
| 1 | Placebo: 62.5% RG755S, 25% RG 752S, 6.25% RG502H, 6.25% 502S | 0 | Rod | Diameter: ~0.257 Length: ~1.43 | ~98.2 |
| 2 | 2 | 20 | Rod | Diameter: ~0.252 Length: ~1.61 | ~103 |
| 3 | 6 | 20 | Rod | Diameter: ~0.256 Length: ~1.51 | ~99.8 |
| 4 | 7 | 20 | Rod | Diameter: ~0.248 Length: ~1.50 | ~101.6 |
| 5 | 8 | 20 | Rod | Diameter: ~0.249 Length: ~1.59 | ~99.1 |

What is claimed is:

1. A method for reducing ocular pressure in an eye of a patient, the method comprising injecting a biodegradable intraocular implant into the anterior chamber of an eye of a patient in need thereof, the biodegradable intraocular implant comprising a biodegradable polymer matrix, polyethylene glycol 3350, and bimatoprost, wherein the bimatoprost and polyethylene glycol 3350 are associated with the biodegradable polymer matrix, which comprises
   a) an ester end poly(D,L-lactide) having an inherent viscosity of 0.25-0.35 dl/g,
   b) an acid end poly(D,L-lactide) having an inherent viscosity of 0.16-0.24 dl/g, and
   c) an ester end poly(D,L-lactide-co-glycolide) having an inherent viscosity of 0.16-0.24 dl/g and a D,L-lactide to glycolide molar ratio of about 75:25;
wherein the bimatoprost comprises 18 to 22% of the biodegradable intraocular implant by weight, the ester end poly(D,L-lactide) comprises 18 to 22% of the biodegradable intraocular implant by weight, the acid end poly(D,L-lactide) comprises 13.5 to 16.5% of the biodegradable intraocular implant by weight, the ester end poly(D,L-lactide-co-glycolide) comprises 36 to 44% of the biodegradable intraocular implant by weight, and wherein the polyethylene glycol 3350 comprises 3.5 to 6.5% of the biodegradable intraocular implant by weight, wherein the inherent viscosity of each of the poly(D,L-lactide) and poly(D,L-lactide-co-glycolide) polymers is determined for a 0.1% solution of the polymer in chloroform at 25° C.

2. The method of claim 1, wherein the bimatoprost comprises 20% of the biodegradable intraocular implant by weight, the ester end poly(D,L-lactide) comprises 20% of the biodegradable intraocular implant by weight, the acid end poly(D,L-lactide) comprises 15% of the biodegradable intraocular implant by weight, the ester end poly(D,L-lactide-co-glycolide) comprises 40% of the biodegradable intraocular implant by weight, and wherein the polyethylene glycol 3350 comprises 5% of the biodegradable intraocular implant by weight.

3. The method of claim 2, wherein the biodegradable intraocular implant is rod-shaped and is formed by a hot-melt extrusion process and wherein the biodegradable intraocular implant is 150 μm to 300 μm in diameter or width, 0.50 mm to 2.5 mm in length, and 30 μg to 100 μg in total weight.

4. The method of claim 2, wherein the biodegradable intraocular implant does not contact the corneal endothelium after placement in the anterior chamber of the eye.

5. The method of claim 2, wherein the biodegradable intraocular implant is effective for reducing intraocular pressure in an eye for 2 months or longer after placement in the anterior chamber of the eye.

6. The method of claim 1, wherein the patient has one or more of elevated intraocular pressure, ocular hypertension, or glaucoma.

7. The method of claim 1, wherein the biodegradable intraocular implant is placed into the anterior chamber using an intraocular delivery apparatus, the apparatus comprising an elongate housing and a cannula extending longitudinally from the housing, the cannula having a proximal end and a distal sharp end and having a lumen extending therethrough, the lumen having an inner diameter sufficient to receive the biodegradable intraocular implant and permit translation of the biodegradable intraocular implant through the lumen and into the anterior chamber of the eye of the patient.

* * * * *